United States Patent [19]

Matsumoto et al.

[11] Patent Number: 5,599,813
[45] Date of Patent: Feb. 4, 1997

[54] THIAZOLOPYRIMIDINE DERIVATIVES

[75] Inventors: Hiroo Matsumoto; Noriko Tanaka; Kiyoshi Nakayama; Haruko Chatani; Michio Iwahana, all of Tokyo, Japan

[73] Assignee: Daiichi Pharmaceutical Co., Ltd., Tokyo, Japan

[21] Appl. No.: 221,577

[22] Filed: Apr. 1, 1994

[30] Foreign Application Priority Data

Apr. 1, 1993 [JP] Japan .................................. 5-110877

[51] Int. Cl.$^6$ ..................... A61K 31/55; A61K 31/505; C07D 513/04
[52] U.S. Cl. .................... 514/232.5; 514/233.2; 514/258; 514/221; 514/368; 544/117; 544/278; 560/21; 560/43; 560/48; 560/126; 560/174; 560/178; 564/440; 540/473; 540/568
[58] Field of Search ................... 544/278, 117; 514/258, 232.5, 233.2

[56] References Cited

PUBLICATIONS

Taylor et al, *Nature* 297 pp. 307–312 (1982).
Folkman et al, *Science* 221, pp. 719–725 (1983).

*Primary Examiner*—Emily Bernhardt
*Attorney, Agent, or Firm*—Sughrue, Mion, Zinn, Macpeak & Seas

[57] ABSTRACT

Thiazolopyrimidine derivatives represented by the formula

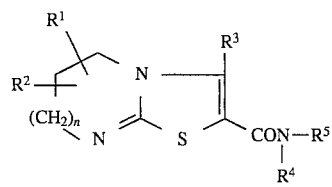

and salts thereof are provided, which are characterized by a carboxamide residue substituted with $R^4$ and $R^5$. The derivatives and salts thereof exhibit antiangiogenic activity and are useful for treatment and cure of diseases, the development of which may be related to angiogenesis, including diabetic retinopathy, various chronic inflammation conditions, growth or metastasis of malignant solid tumors, rheumatism and psoriasis.

13 Claims, No Drawings

THIAZOLOPYRIMIDINE DERIVATIVES

FIELD OF THE INVENTION

This invention relates to novel thiazolopyrimidine derivatives and salts thereof which exhibit antiangiogenic activity. The compounds are useful for treatment and cure of diseases, the development of which may be related to angiogenesis. Examples of such diseases include diabetic retinopathy, various chronic inflammation conditions, growth or metastasis of malignant solid tumors, rheumatism and psoriasis.

BACKGROUND OF THE INVENTION

The term "antiangiogenic" as used herein means having the activity of suppressing the formation of new blood vessels. Amgiogenesis is related to several pathological conditions such as diabetic retinopathy, growth and metastasis of solid tumors, and various inflammation conditions including rheumatism, psoriasis and the like.

Accordingly, research on antiangiogenic compounds has been undertaken and reported. Such reports include research on, for example, protamine (Nature, 297:307, 1982), a combination of heparin with cortisone acetate (Science, 221:719, 1983), fumagillin and its derivatives, and the like.

In addition, α-interferon is reported to have antiangiogenic activities and to act well on infantile lethal angiosarcoma.

However, these compounds were found to have problems with activity, maintenance of activity and side effects such as cytotoxicity, fever, bleeding and the like.

SUMMARY OF THE INVENTION

An object of the invention is to provide novel compounds having excellent antiangiogenic activity.

The present inventors have conducted extensive studies for the the purpose of obtaining compounds with more excellent activity and higher safety, and have found that thiazolopyrimidine derivatives exhibit excellent antiangiogenic characteristics.

The present invention provides compounds represented by the following general formula

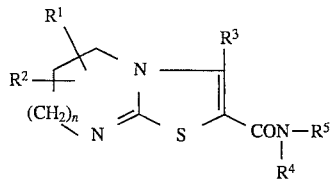

wherein n represents an integer of 1 to 3;
$R^1$ and $R^2$ represent independently a hydrogen atom or an alkyl group having from 1 to 6 carbon atoms;
$R^3$ represents a hydroxyl group, an alkyl group having from 1 to 12 carbon atoms, a cycloalkyl group having from 3 to 6 carbon atoms, a halogenoalkylgroup having from 1 to 6 carbon atoms, a cyanoalkyl group having from 2 to 7 carbon atoms, an alkoxyalkyl group having from 2 to 12 carbon atoms, an alkoxycarbonylalkyl group having from 3 to 10 carbon atoms, a carboxyalkyl group having from 2 to 7 carbon atoms, an alkoxyl group having from 1 to 12 carbon atoms, a cycloalkoxyl group having from 3 to 6 carbon atoms, an alkoxyalkoxyl group having from 2 to 9 carbon atoms, an alkoxycarbonylalkoxyl group having from 3 to 10 carbon atoms, a carboxyalkoxyl group having from 2 to 4 carbon atoms, an alkenylalkoxyl group having from 3 to 6 carbon atoms or an aryl group;
$R^4$ and $R^5$ represents independently a hydrogen atom, an alkyl group having from 1 to 18 carbon atoms, an alkoxycarbonylalkyl group having from 3 to 7carbon atoms, a carboxyalkyl group having from 2 to 4 carbon atoms, a cyanoalkyl group having from 2 to 4 carbon atoms, a hydroxyalkyl group having from 1 to 3 carbon atoms, an alkenyl group having from 2 to 18 carbon atoms, a cycloalkyl group having from 3 to 6 carbon atoms, a phenylsulfonyl group or a group of formula:

$$—(CH_2)_a—Q$$

wherein $a$ represents an integer of 0 to 6;
Q represents an aryl group, a saturated or unsaturated 5 to 8 membered heterocyclic group, a condensed ring group composed of a benzene ring and a heterocyclic ring, the Q may contain simultaneously or independently 1 to 3 substitution groups selected from a halogen atom, a nitro group, a sulfo group, a group of formula:

$$—X—(CH_2)_b—COOR^6$$

or a group of formula:

$$—X—(CH_2)_b—Y—(CH_2)_c—CH_3$$

wherein X represents a single-bond, an oxygen atom, a sulfur atom, a sulfonyl group or an aryl group;
Y represents a single-bond, an oxygen atom; or an aryl group
$R^6$ represents a hydrogen atom or an alkyl group having from 1 to 3 carbon atoms;
b and c each represents an integer of 0 to 6; if X is an aryl group, then $—(CH_2)_b—$, $COOR^6$ (when b is 0) or Y (when b is 0) may be substituted at any position of said aryl group, if Y is an aryl group, then $—(CH_2)_c—$ or $CH_3$ (when c is 0) may be substituted at any position of said aryl group, or salts thereof.

DETAILED DESCRIPTION OF THE INVENTION

The term "alkyl group" as used herein means a straight or branched chain alkyl group and includes, for example, methyl, ethyl, n-propyl, isopropyl, n-butyl and the like.

The term "cycloalkyl group" as used herein means a cycloalkyl group having 3 to 6 carbon atoms and includes, for example, cyclopropyl, cyclobutyl, cyclohexyl, cyclopentyl and the like.

The term "halogenoalkyl group" as used herein means an alkyl group substituted with a halogen atom and includes, for example, chloromethyl, bromoethyl, dichloromethyl, trifluoromethyl and the like. The halogen atom may be linked to any carbon atom in the alkyl group.

The term "cyanoalkyl group" as used herein means an alkyl group substituted with a cyano group. The cyano group may be linked to any carbon atom in the alkyl group.

The term "alkoxyl group" as used herein includes, for example, methoxyl, ethoxyl, propoxyl, butoxyl and the like.

The alkyl group in an alkoxyl group may be a straight or branched chain.

The term "cycloalkoxyl group" as used herein means a cycloalkoxyl group having 3 to 6 carbon atoms.

The term "alkenyl group" as used herein means a straight or branched chain alkenyl group and includes, for example, vinyl, allyl, isopropenyl, 2-butenyl, 3-butenyl, 1-methylallyl and the like.

The term "alkoxyalkyl group" as used herein means an alkyl group substituted with an alkoxyl group and includes, for example, methoxymethyl, ethoxymethyl, methoxyethyl, ethoxyethyl and the like. The alkoxyl group may be linked to any carbon atom in the alkyl group.

The term "alkoxycarbonylalkyl group" as used herein means an alkyl group substituted with a straight or branched chain alkoxycarbonyl group having 1 to 3 carbon atoms and includes, for example, ethoxycarbonylethyl, ethoxycarbonylpropyl and the like. The alkoxycarbonyl group may be linked to any carbon atom in the alkyl group.

The term "carboxyalkyl group" as used herein means an alkyl group substituted with a carboxyl group and includes, for example, carboxypropyl and the like. The carboxyl group may be linked to any carbon atom in the alkyl group.

The term "alkoxyalkoxyl group" as used herein means an alkoxyl group substituted with an alkoxyl group and includes, for example, methoxymethoxyl, ethoxymethoxyl, methoxyethoxyl and the like. The alkoxyl group may be linked to any carbon atom of the alkyl chain in the alkoxyl group.

The term "alkoxycarbonylalkoxyl group" as used herein means an alkoxyl group substituted with a straight or branched alkoxycarbonyl group having 1 to 3 carbon atoms and includes, for example, methoxycarbonylmethoxyl, 1-methoxycarbonylethoxyl, 2-methoxycarbonylethoxyl and the like. The alkoxycarbonyl group may be linked to any carbon atom of the alkyl chain in the alkoxyl group.

The term "carboxyalkoxyl group" as used herein means an alkoxyl group substituted with a carboxyl group and includes, for example, carboxyethoxyl, carboxypropoxyl and the like. The carboxyl group may be linked to any carbon atom of the alkyl chain in the alkyl group.

The term "alkenylalkoxyl group" as used herein means an alkoxyl group substituted with an alkenyl group and includes, for example, vinylmethoxyl, vinylethoxyl, allylmethoxyl, allylethoxyl, and the like. The alkenyl group may be linked to any carbon atom of the alkyl chain in the alkoxyl group.

The term "hydroxyalkyl group" as used herein means an alkyl group substituted with a hydroxyl group which may be linked to any carbon atom in the alkyl group.

The term "aryl group" as used herein contains 6 to 12 carbon atoms and includes, for example, phenyl, biphenyl, naphthyl and the like.

The term "heterocyclic group" as used herein means a substituent group which is derived from a 5- to 8-membered heterocyclic ring containing 1 to 4 hetero atoms such as nitrogen, sulfur or oxygen, and includes, for example, pyridyl, pyrazinyl, oxazolyl, thiazolyl, thiadiazolyl, imidazolyl, pyrrolidinyl, piperidyl, morpholinyl and the like.

The term "condensed ring group" as used herein means a substitutent group which is derived from a condensed ring group composed of a benzene ring and a heterocyclic ring which has the same definition as described above, and includes, for example, benzoxazolyl, benzothiazolyl, benzothiadiazolyl and the like.

The abovementioned aryl, heterocyclic and condensed ring groups may be substituted with a halogen atom, a nitro group, a sulfo group, a group of formula, —X—(CH$_2$)$_b$—COOR$^6$ or a group of formula, —X—(CH$_2$)$_b$—Y—(CH$_2$)$_c$—CH$_3$, wherein X represents a single-bond, an oxygen atom, a sulfur atom, a sulfonyl group, an aryl group; Y represents a single-bond or an oxygen atom; or an aryl group R$^6$ represents a hydrogen atom or an alkyl group having from 1 to 3 carbon atoms; b and c each represents an integer of 0 to 6; if X is an aryl group, then —(CH$_2$)$_b$—, COOR$^6$ (when b is 0) or Y (when b is 0) may be substituted at any position of said aryl group, if Y is an aryl group, then —(CH$_2$)$_c$— or CH$_3$ (when c is 0) may be substituted at any position of said aryl group.

The term "halogen atom" as used herein includes, for example, florine, chlorine, bromine and iodine.

A reaction scheme for the production of the compounds of this invention is shown below using a thiazolopyrimidine compound (n=1) as an example.

Depending on the nature of the substituent R$^3$, it is advantageous to use a different process as explained hereinafter. Compounds in which n=2 or 3 can be produced in the same manner as in the case of n=1.

When the substituent R$^3$ is a hydroxyl group or an alkoxyl group (R$^1$, R$^2$, R$^4$ and R$^5$ are defined above. X represents a halogen atom)

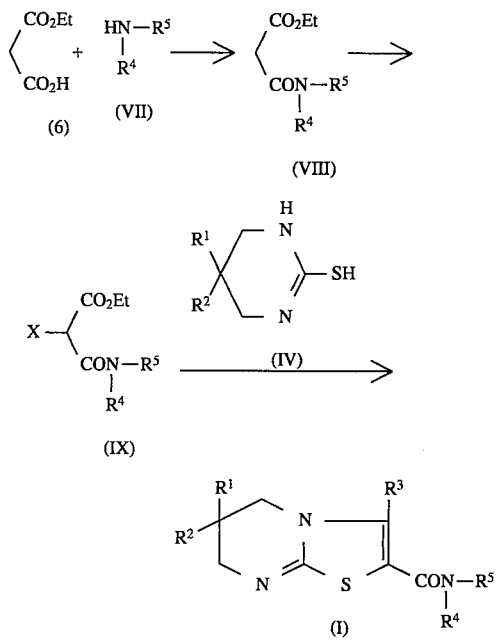

Condensation (VII→VIII)

The compounds of the formula (VIII) can be obtained by reacting reactive derivatives derived from known carboxylic acids of the formula (6) with an amine of the formula (VII).

Examples of the reactive derivatives include an active ester or an acid halide of carboxylic acid. Examples of the acid halide include fluoride, chloride, bromide and iodide, preferably chloride.

Examples of the halogenation reagent include thionyl chloride, phosphonyl chloride, phosphorus pentachloride, phophorus trichloride and the like.

The reaction is carried out in an appropriate solvent such as chloroform, dichloromethane, acetonitrile, dimethylformamide and the like. The reaction can be carried out at a temperature of from 0° to 100° C. The reaction is completed in the range of from about 10 minutes to 10 hours and usually from 30 minutes to 2 hours.

Another process for the preparation of compound (VIII) comprises reacting a carboxylic acid of the formula (6) with an amine of the formula (VII) in the presence of a condensing reagent such as N,N'-dicyclohexylcarbodiimide.

Halogenation (VIII→IX)

The compounds of formula (IX) can be obtained by chlorinating the compounds of formula (VIII) with sulfurylchloride or N-chlorosuccinimide, or by brominating with bromide.

The reaction is carried out in an appropriate solvent such as diethylether, carbon tetrachloride and the like. The reaction can be carried out at a temperature of from 0° C. to room temperature. The reaction usually is complete in the range of from about 15 minutes to 6 hours.

The halogenation reagent may be used preferably in an amount of from 1.0 to 1.5 equivalents to the compound of formula (VIII). The compound of formula (IX) can be purified by known methods such as extraction, recrystallization or column chromatography, but it can be used in the following reaction without purification in many case.

Condensation ring-closing reaction (IX→I)

Compounds of formula (I) having a hydroxyl group at R3 can be obtained by a condensation ring-closing reaction of the compounds of formula (IX) and pyrimidine-2-thiol of the formula (IV) or a tautomer thereof.

The reaction is preferably carried out in the presence of a solvent inert to the reaction. Examples of such solvents include aromatic hydrocarbons such as benzene, toluene, xylene; alcohols such as methanol, ethanol, propanol; methylethylketone; dioxane and the like. The reaction can be carried out at a temperature of from room temperature to 180° C. The reaction usually is complete in the range of from about 1 hour to 48 hours.

Compounds of formula (I) having an alkoxyl group at $R^3$ can be obtained by reacting a compound of formula (I) having a hydroxyl group at $R^3$ with an alcohol in the presence of a complex of diethylazodicarboxylate and triphenylphosphin.

The reaction is preferably carried out in the presence of a solvent inert to the reaction. Examples of such solvents include aromatic hydrocarbons such as benzene, toluene, xylene; ethers such as dioxane, diethylether, tetrahydrofuran and the like. The reaction can be carried out at a temperature of from −80° C. to room temperature. The reaction usually is complete in the range of from about 30 minutes to 12 hours.

The compounds of the present invention having a carboxyl group, in which $R^3$ is a carboxyalkyl group or a carboxyalkoxyl group, $R^4$ or $R^5$ is a carboxyalkyl group or $R^6$ is a hydrogen atom, can be obtained by hydrolyzing the corresponding compounds having an ester residue in the presence of an inorganic base using a solvent.

Examples of inorganic bases include sodium hydroxide, potassium hydroxide and the like.

The inorganic bases may be used in an amount of from 2 to 10 molar equivalent to the ester compound.

Examples of the solvent include lower alcohols such as methanol, ethanol and the like.

The reaction can be carried out at a temperature of from room temperature to 180° C. and preferably from 80° C. to 100° C. The reaction usually is complete in the range of from about 1 hour to 24 hours.

The reaction also can be carried out under acidic conditions, using hydrochloric acid, hydrobromic acid, trifluoroacetic acid or the like, at from 0° C. to 100° C., and in the range of from 1 hour to 48 hours.

When the substituent $R^3$ is other than a hydroxyl group or an alkoxyl group ($R^1$, $R^2$, $R^4$ and $R^5$ are defined above. R' represents alkyl)

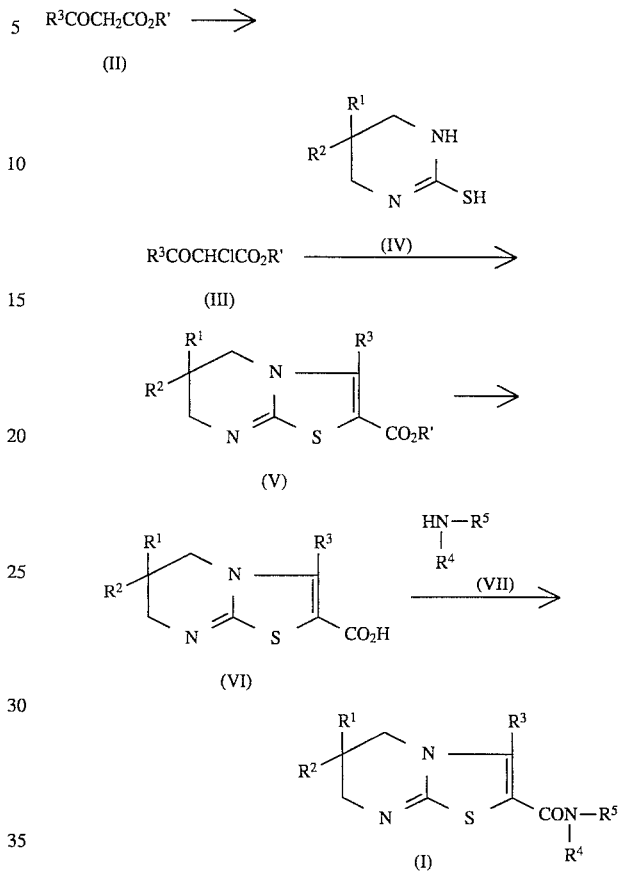

Chlorinating (II→III)

The compounds of general formula (III) can be derived by a chlorinating reaction of a β-ketoester of the formula (II) with a chlorinating agent such as sulfurylchloride or N-chlorosuccinimide.

The reaction is carried out in an appropriate solvent such as diethylether, carbon tetrachloride and the like. The reaction can be carried out at a temperature of from 0° C. to room temperature. The reaction usually is complete in the range of from about 15 minutes to 6 hours.

The chlorinating agent may be used in an amount of from 1.0 to 1.5 equivalents to the compounds of formula (II). The resulting compound of formula (III) can be purified by known methods such as extraction, recrystallization or column chromatography, but it can be used in the following reaction without purification in many cases.

Condensation ring-closing reaction (III→V) and Hydrolysis (V→VI)

Thiazolopyrimidine-2-carboxylates of formula (V) can be obtained by a condensation ring-closing reaction of the compounds of formula (III) and pyrimidine-2-thiol of formula (IV) or a tautomer thereof.

The reaction product of thiazolopyrimidine-2-carboxylate of formula (V) may be isolated and purified as disclosed in Example 11.

Thiazolopyrimidine-2-carboxylic acid of formula (VI) can be prepared by hydrolysis of thiazolopyrimidine-2-carboxylate of formula (V).

The condensation ring-closing reaction is preferably carried out in the presence of a solvent inert to the reaction. Examples of such solvents include aromatic hydrocarbons such as benzene, toluene, xylene; alcohols such as methanol, ethanol, propanol; methylethylketone; dioxane and the like.

The condensation ring-closing reaction can be carried out at a temperature of from room temperature to 180° C. and the reaction usually is complete in the range of from about 1 hour to 48 hours.

The hydrolysis reaction can be carried out under basic condition using an inorganic base such as sodium hydroxide, potassium hydroxide and the like, or under acidic conditions using hydrochloric acid, hydrobromic acid and the like.

Another process of preparing thiazolopyrimidine-2-carboxylic acid of formula (VI) comprises reacting the compounds of formula (III) with pyrimidine-2-thiol of formula (IV) or a tautomer thereof in the presence of hydrogen chloride or hydrogen bromide in a solvent.

Under this condition, the condensation ring-closing reaction and the following hydrolysis can be carried out together.

Examples of such solvents include lower alcohols such as methanol, ethanol, propanol; dioxane and the like.

In this case, the reaction can be carried out at a temperature of from room temperature to 100° C. The reaction usually is comlete in the range of from about 1 hour to 12 hours.

Condensation (VI→I)

The compounds of the present invention can be obtained by reacting the reactive derivatives derived from the carboxylic acid of formula (VI) with an amine of formula (VII).

Examples of the reactive derivatives include active esters or acid halides of carboxylic acids.

The reaction is carried out preferably under anhydrous conditions. The solvent to be used is preferably pyridine, but depending upon the kind of acidic halide, a mixed solvent of pyridine and dimethylformamide or acetonitrile is used.

The reaction is carried out in the presence of a catalyst such as dimethylaminopyridine, at a temperature of from room temperature to 180° C., preferably 80° C. to 100° C., and in the range of from 1 hour to 48 hours.

Examples of the acid halide include fluoride, chloride, bromide and iodide, preferably chloride.

Examples of the halogenation reagent include thionyl chloride, phosphonyl chloride, phosphorus pentachloride and phophorus trichloride.

Another process for the preparation of the compounds of the present invention of formula (I) comprises reacting a carboxylic acid of formula (VI) with an amine of the formula (VII) in the presence of a condensing agent such as N,N'-dicyclohexylcarbodiimide.

In the above series of reactions, the product obtained in each reaction can be isolated or purified by known methods such as extraction, recrystallization or column chromatography.

The free form of the compound of formula (I) can be obtained by neutralization of the salt of the compound obtained in the process with an appropriate amount of an inorganic base.

Examples of the inorganic base include sodium hydroxide, potassium hydroxide, potassium carbonate, sodium hydrogencarbonate and the like.

If necessary, the salt of this compound can be converted into the corresponding pharmaceutically acceptable acid addition salt by using hydrochloric acid, hydrobromic acid, phosphoric acid, oxalic acid, citric acid, malic acid and the like.

The starting material of formula (II) (R3 is defined above as other than a hydroxyl group or an alkoxyl group and R' is defined above), is a known compound in many cases, and it can be derived by a reaction according to a known method (J. Org. Chem. Vol. 1. 43, 2087 (1978) or J. Med. Chem. Vol. 1. 32, 1571 (1898) ).

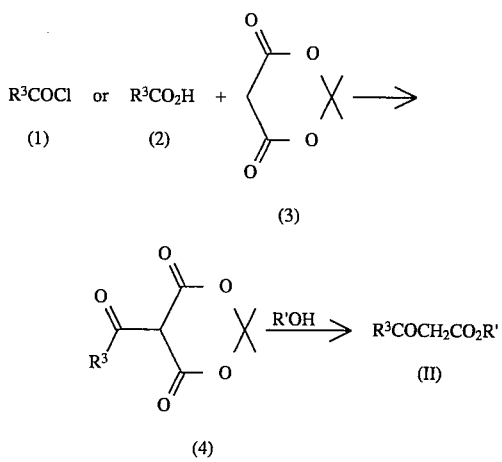

A starting material of formula (IV) ($R^1$ and $R^2$ are defined above), include known compounds and can be derived by a known method (Org. Soc. Coll. Vol. 3, 394 or J. Med. Chem. 18(5) 447 (1975)).

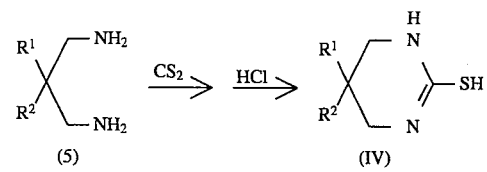

Many amines of the formula (VII) ($R^4$ and $R^5$ are defined above) are known compounds. Biphenyl compounds of the formula (VII) can be derived by reaction according to a known method (Tetrahedron Letter, Vol. 26, No. 49, 5997 (1985)).

The compounds of the present invention exhibit antiangiogenic activities and are useful as a preventive medicine for various inflammation diseases, growth and metastasis of solid tumors, rheumatism, psoriasis, diabetic retinopathy, retrolental fibroplasia, vascularization associated with keratoplasty and arteriosclerosis.

Dosage forms of the pharmaceutical preparations containing the compound of the present invention are appropriately selected according to the administration route and can be prepared by conventional methods. Examples of dosage forms for oral administration include tablets, powders, granules, capsules, solutions, syrups, elixirs, and oily or aqueous suspensions.

Injectable preparations may contain adjuvants, such as stabilizers, antiseptics, and solubilizers. The injectable solution which may contain these adjuvants may be put into a container and solidified by, for example, lyophilization to prepare a solid preparation which is dissolved on use. The container may contain either a single dose or multiple doses.

Preparations for external application include solutions, suspensions, emulsions, ointments, gels, creams, lotions, and sprays.

Solid preparations may contain, in addition to the active compound, pharmaceutically acceptable additives. For example, the active compound is mixed with additives selected according to need from fillers, extenders, binders, disintegrators, absorption accelerators, wetting agents, and lubricants and formulated into solid preparations.

Liquid preparations include solutions, suspensions, and emulsions. They may contain adjuvants, such as suspending agents, emulsifiers, and so forth.

These compounds and preparations can be used with other compounds exhibiting antiangiogenic activities.

Examples of such other compounds include a sulfated polysaccharide such as DS-4152 and the like; steroids which having antiangiogenic activities and fumagillin derivatives.

The compound of the present invention may be used at a dosage of 1 to 300 mg in an adult human per m² of body surface area per day, though varying by more or less depending on the disease and the symptoms.

This invention will hereinafter be described further by the following Examples and Reference Examples. However, the invention is not liminted thereto.

REFERENCE EXAMPLE 1 tert-Butyl 3-cyclobutyl-3-oxopropionate

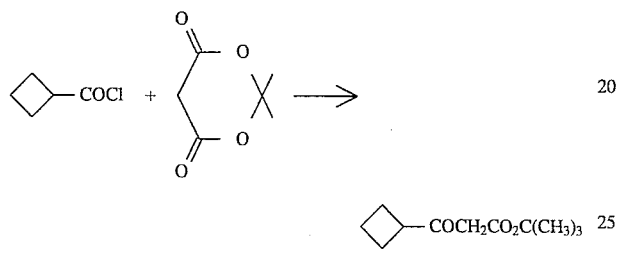

In a mixture of 100 ml of dichloromethane and 15 ml of pyridine was dissolved 12.2 g of meldrum's acid. Under cooling with ice, 10.0 g of cyclobutane carboxychloride was added dropwise to the solution, followed by stirring under room temperature for 2 hours. The solvent was removed under reduced pressure and to the residue was added water. The mixture was extracted with ethyl acetate. The extract was washed with 1N hydrochloric acid and dried over anhydrous magnesium sulfate. The solvent was removed under reduced pressure. The residue was dissolved in 100 ml of tert-butanol and the solution was heated under reflux for 5 hours. The solvent was removed under reduced pressure and the residue was subjected to column chromatography using 100 g of silica gel. The oily titled compound (7.8 g) was obtained from a chloroform eluate fraction.

$^1$H-NMR(CDCl$_3$) δ (ppm):
1.47(9H, s), 1.80–2.25(6H, m), 3.30(2H, s).

REFERENCE EXAMPLE 2 tert-Butyl 3-oxononanoate

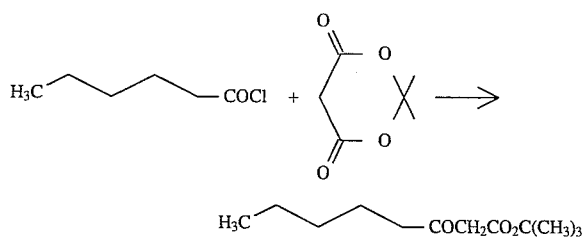

In a mixture of 100 ml of dichloromethane and 32 ml of pyridine was dissolved 25.0 g of meldrum's acid. Under cooling with ice, 10.0 g of hexanoyl chloride was added dropwise to the solution, followed by stirring under room temperature for 1 hour. The solvent was removed and to the residue was added water. The mixture was extracted with ethyl acetate. The extract was washed with 1N hydrochloric acid and dried over anhydrous magnesium sulfate. The solvent was removed under reduced pressure and the residue was dissolved in 100 ml of tert-butanol, followed by reflux under heating for 3 hours. The solvent was removed under reduced pressure. The residue was subjected to distillation under reduced pressure to yield 22.0 g of the oily titled compound.

Boiling Point 90°–95° C. (3 mmHg) $^1$H-NMR(CDCl$_3$) δ (ppm): 0.89(3H, t), 1.49(9H, s), 1.25–2.53(8H, m), 3.34(2H, s).

REFERENCE EXAMPLE 3 tert-Butyl 4-methyl-3-oxopentanoate

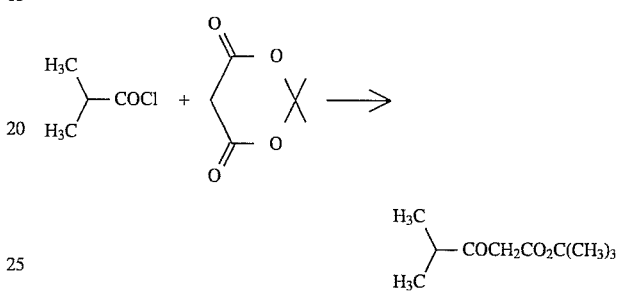

In a mixture of 85 ml of dichloromethane and 40 ml of pyridine was dissolved 33.8 g of meldrum's acid. Under cooling with ice, 25.0 g of isobutyl chloride was added dropwise to the solution, followed by stirring under room temperature for 1 hour. The solvent was removed under reduced pressure and to the residue was added water. The mixture was extracted with ethyl acetate. The extract was washed with 1N hydrochloric acid and dried over anhydrous magnesium sulfate. The solvent was removed under reduced pressure and the residue was dissolved in 100 ml of tert-butanol, followed by reflux under heating for 4 hours. The solvent was removed under reduced pressure. The residue was subjected to distillation under reduced pressure to yield 32.5 g of the oily titled compound.

Boiling Point 68°–76° C. (4 mmHg) $^1$H-NMR(CDCl$_3$) δ (ppm): 1.13(6H, d), 1.47(9H, s), 2.27(1H, m), 3.40(2H, s).

REFERENCE EXAMPLE 4 tert-Butyl 5-ethoxycarbonyl-3-oxopentanoate

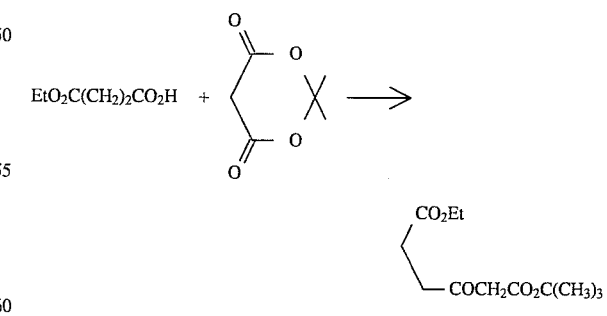

In 400 ml of dichloromethane were dissolved 16.7 g of 5-ethoxycarbonyl propionic acid, 16.47 g of meldrum's acid and 20.94 g of 3,5-dimethylaminopyridine. Under cooling with ice, to the mixture was added 25.94 g of N,N'-dicyclohexylcarbodiimide, followed by stirring under room temperature for 2 hours. Insoluble materials were removed by filtration. The solvent was removed under reduced pressure and to the residue was added water, followed by extracting with ethyl acetate. The extract was washed with 1N hydrochloric acid and dried over anhydrous magnesium sulfate. The solvent was removed under reduced pressure. The resulting substance was dissolved in 250 ml of tert-butanol, followed by heating under reflux for 12 hours. The solvent was removed under reduced pressure. The residue was subjected to column chromatography (silica gel: 250 g). The oily titled compound (24.7 g) was obtained from an n-hexane-ethyl acetate (5:1 v/v) eluate fraction.

$^1$H-NMR(CDCl$_3$) δ (ppm): 1.27(3H, t), 1.49(9H, s), 2.26(2H, t), 2.88(2H, t), 3.42(2H, s), 4.16(2H, q).

REFERENCE EXAMPLE 5

N-(2-Etoxycarbonylethyl)-3,5-dichloroaniline

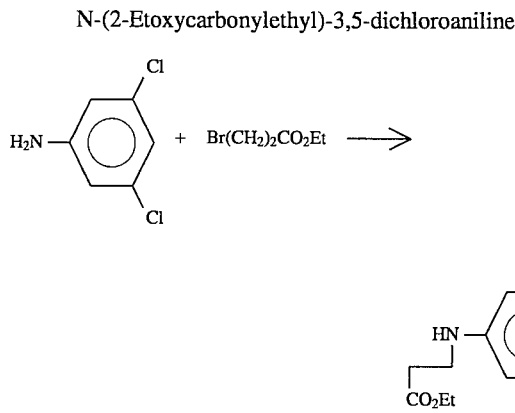

In 20 ml of dimethylformamide was dissolved 5.0 g of 3,5-dichloroaniline. To the solution was added 6.16 g of ethyl 3-bromopropionate, followed by heating under reflux for 6 hours. The reaction mixture was concentrated and the concentrate was extracted with ethyl acetate. The extract was washed with saturated sodium hydrogencarbonate aqueous solution and saturated sodium chloride aqueous solution and dried over anhydrous magnesium sulfate. The solvent was removed under reduced pressure. The residue was subjected-to silica gel column chromatography (eluent: chloroform:hexane=1:1) to yield 3.98 g of the titled compound as a white crystal.

Melting Point 72°–74° C. $^1$H-NMR(CDCl$_3$) δ (ppm): 1.27(3H, t), 2.58(2H, t), 3.40(2H, t), 4.12(2H, q), 6.46(2H, d), 6.67(1H, t).

REFERENCE EXAMPLE 6

4-n-Heptylthioaniline

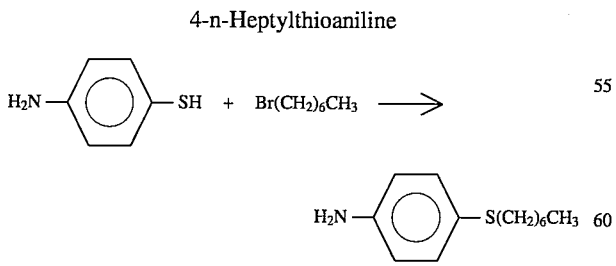

In 100 ml of acetonitrile was dissolved 5.90 g of 4-aminothiophenol. To the solution were added 6.57 ml of triethylamine and 8.44 g of n-heptylbromide, followed by stirring at room temperature for 18 hours. The precipitated crystals were collected by filtration, followed by removing the solvent. To the residue was added water and the mixture was extracted with ethyl acetate. The extract was washed successively with 1N sodium hydroxide aqueous solution and saturated sodium chloride aqueous solution and dried over anhydrous potassium carbonate. After removing the solvent, the residue was purified by silica gel column chromatography using 50 g of silica gel and using chloroform as eluent to obtain 6.06 g of the titled compound.

$^1$H-NMR(CDCl$_3$) δ (ppm): 0.8–0.95(3H, m), 0.9–1.7(10H, m), 2.76(2H, t), 3.61(2H, brs), 6.59(2H, dd), 7.21(2H, dd).

REFERENCE EXAMPLE 7

4-n-Heptylsulfonylaniline

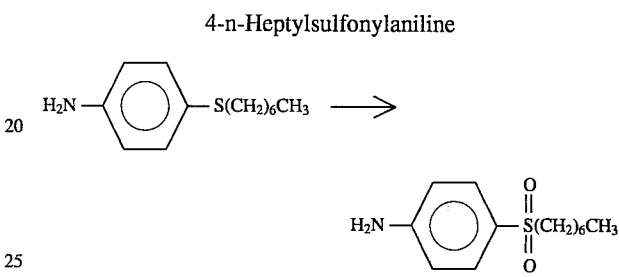

In 50 ml of dichloromethane was dissolved 2.17 g of 4-n-heptyl-thioaniline obtained in Reference Example 6. To the solution was added 5.53 g of m-chloroperbenzoic acid in limited amounts under ice-cooling, followed by stirring at room temperature for 6.5 hours. To the reaction mixture was added saturated sodium hydrogencarbonate aqueous solution. The mixture was extracted with chloroform. The extract was washed with saturated sodium chloride aqueous solution and dried over anhydrous potassium carbonate, followed by removing the solvent. The residue was purified by silica gel column chromatography using 30 g of silica gel to yield 0.97 g of the titled compound.

Melting Point 91°–92° C. $^1$H-NMR(CDCl$_3$) δ (ppm): 0.7–1.0(3H, m), 1.0–1.8(10H, m), 2.9–3.2(2H, m), 4.4(2H, brs), 6.69(2H, d), 7.60(2H, d).

REFERENCE EXAMPLE 8

Methyl 3'-nitro-biphenyl-4-carboxylate

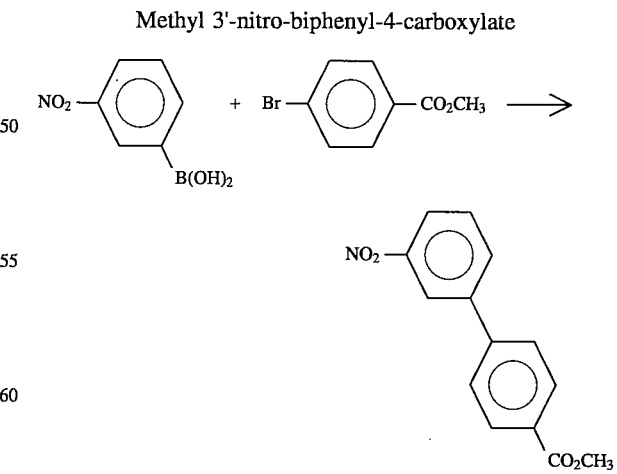

In 60 ml of toluene was dissolved 6.4 g of 4-bromophenylacetic acid. To the solution were added 1.04 g of tetrakistriphenylphosphine palladium and 30 ml of 2M sodium carbonate aqueous solution. To the mixture was added the solution of 5.0 g 3-nitrophenylboric acid in 15 ml of methanol under a stream of nitrogen, followed by stirring at 80° C. for 11 hours. The reacton mixture was diluted with chloroform and filtered by Celite. The organic layer was separated and washed with 2M sodium carbonate aqueous solution and dried over anhydrous magnesium sulfate. After removing the solvent, the residue was dissolved in methanol under heating. The mixture was treated with active carbon and cooled to precipitate crystals. The crystals were collected by filtration and dried over anhydrous magnesium sulfate to yield 3.8 g of the titled compound.

Melting Point 136°–141° C. $^1$H-NMR(CDCl$_3$) δ (ppm): 3.96(3H, s), 7.65(1H, t), 7.70(2H, d), 7.95(1H, m), 8.16(2H, d), 8.25(1H, m), 8.47(1H, m).

Elementary Analysis for $C_{14}H_{11}NO_4$ Calcd.: C,65.37; H,4.31; N,5.45. Found: C,65.36; H,4.30; N,5.60.

REFERENCE EXAMPLE 9

Metyl 3'-amino-biphenyl-4-carboxylate

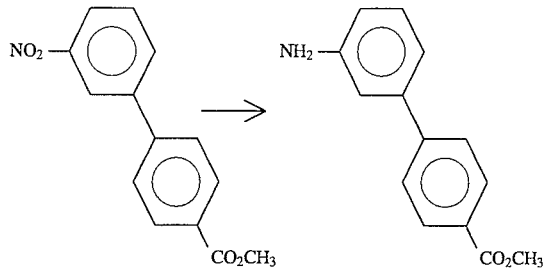

In 100 ml of tetrahydrofuran was dissolved 2.70 g of methyl 3'-nitro-biphenyl-4-carboxylate obtained in Reference Example 8. To the solution was added 1.0 g of 10% palladium-on-carbon and the mixture was subjected to catalytic reduction for 2 hours. After removing the catalyst by filtration, the solvent was removed under reduced pressure to obtain 2.34 g of the titled compound.

Melting Point 145°–148° C. $^1$H-NMR(CDCl$_3$) δ (ppm): 3.93(3H, s), 6.73(1H, m), 6.93(1H, m), 7.03–7.34(2H, m), 7.63(2H, m), 8.08(2H, m).

Elementary Analysis for $C_{14}H_{13}NO_2$ Calcd.: C,73.99; H,5.77; N,6.16. Found : C,74.04 ; H,5.93 ; N,6.19.

REFERENCE EXAMPLE 10

Etyl 2-(3,5-dichlorophenylaminocarbonyl)acetate

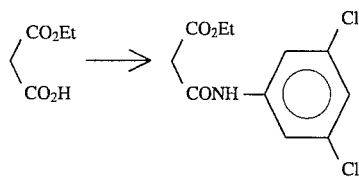

In 200 ml of dichloromethane were dissolved 5.0 g of monoethyl malonate and 6.12 g of 3,5-dichloroaniline. Under cooling with ice, to the solution was added 8.57 g of N,N'-dicyclohexylcarbodiimide, followed by stirring at room temperature for 5 hours. Insoluble materials was removed by filtration. The filtrate was diluted with ethyl acetate and washed with 1N hydrochloric acid and dried over anhydrous magnesium sulfate. The residue was purified by silica gel column chromatography using 250 g of silica gel and using chloroform-acetone (20:1 by volume) as an eluent to obtain 6.57 g of the oily titled compound.

$^1$H-NMR(CDCl$_3$) δ (ppm): 1.33(3H, t), 3.47(2H, s), 4.26(2H, q), 7.10(1H, t), 7.53(2H, d).

EXAMPLE 1

3-Cyclobutyl-6,7-dihydro-5H-thiazolo[3,2-a]-pyrimidine-2-carboxylic acid hydrochloride

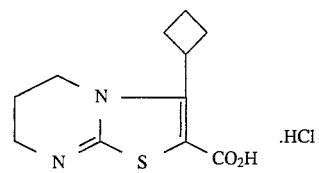

In 100 ml of dry diethylether was dissolved 10 g of tert-butyl 3-cyclobutyl-3-oxopropionate obtained in Reference Example 1. To the solution was added dropwise 6.8 ml of sulfuryl chloride under cooling with ice. After stirring at room temperature for 30 minutes, the reaction mixture was added into saturated sodium hydrogencarbonate aqueous solution and the organic layer was separated. The organic layer was washed with saturated sodium chloride aqueous solution, dried over anhydrous magnesium sulfate and the solvent was removed under reduced pressure to yield an oily residue. This was used in the following step without purification. 9.4 g of the residue was dissolved into 200 ml of isopropylalcohol. To the solution was added 5 g of 3,4,5,6-tetrahydro-2-pyrimidine-thiol and the mixture was refluxed under heating for 3 hours. To the mixture was added 100 ml of saturated hydrogenchloride isopropylalcohol solution, followed by stirring under heating for 2 hours. After cooling, to the reaction mixture was added diethylether to precipitate. The crystals were collected by filtration, and washed with acetone to obtain 7.8 g of the titled compound.

Melting Point 198°–200° C. $^1$H-NMR(D$_2$O) δ (ppm): 1.60–2.30(6H, m), 2.20(2H, t), 3.50, 4.15(each 2H, t).

Elementary Analysis for $C_{11}H_{14}N_2O_2S \cdot HCl$ Calcd.: C,48.03; H,5.50; N,10.20. Found: C,48.36; H,5.31; N,9.94.

EXAMPLE 2

N-(3,5-Dichlorophenyl)-3-cyclobutyl-6,7-dihydro-5H-thiazolo[3,2-a]pyrimidine-2-carboxamide hydrochloride

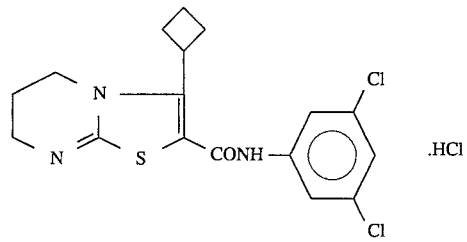

To 20 ml of thionyl chloride was suspended 5.0 g of 3-cyclobutyl-6,7-dihydro-5H-thiazolo[3,2-a]pyrimidine-2-carboxylic acid obtained in Example 1, followed by reflux under heating for 30 minutes. Under cooling, an anhydrous diethylether was added dropwise to the reaction mixture to precipitate. The crystals were collected by filtration and washed with anhydrous diethylether to yield 5.4 g of 3-cyclobutyl-6,7-dihydro-5H-thiazolo[3,2-a]pyrimidine-2-carbonyl chloride as a pale yellow crystals. To the mixture of 60 ml of pyridine and 20 ml of dimethyl formamide was suspended 2.7 g of the crystal. To the mixture was added 1.5 g of 3,5-dichloroaniline and 60 mg of dimethylaminopyridine, followed by stirring at 70° C. for 17 hours. The solvent was removed under reduced pressure to obtain a residue. Addition of water to the residue caused precipitation of the crystals and the crystals were collected by filtration. After washing with cold methanol, the crystals were suspended to saturated hydrogenchloride ethanol solution. After washing with diethylether, the crystals were collected by filtration to obtain 1.2 g of the titled compound.

Melting Point 305°–307° C. $^1$H-NMR(DMSO-$d_6$: CDCl$_3$(20:1)) δ (ppm): 1.70–2.50(6H, m), 2.28(2H, t), 3.00(2H, t), 3.60, 4.00(each 2H,t), 3.80(1H, m), 7.40–7.80(3H, m).

Elementary Analysis for $C_{17}H_{17}N_3OSCl_2.HCl$ Calcd.: C,48.75 ; H,4.33 ; N,10.03. Found: C,48.71; H,4.27; N,10.33.

The following compounds of Example 3 to 10 were prepared in a similar manner as described in Reference Example 1, Example 1 and Example 2.

EXAMPLE 3

N-(3,5-Dichlorophenyl)-3-cyclohexyl-6,7-dihydro-5H-thiazolo-[3,2-a]pyrimidine-2-carboxamide hydrochloride Melting Point 288°–293° C.

Elementary Analysis for $C_{16}H_{21}Cl_2N_3O_3S.HCl$ Calcd.: C,51.07; H,4.96; N,9.40. Found: C,50.96; H,4.82; N,9.13.

EXAMPLE 4

N-(3,5-Dichlorophenyl)-3-cyclopropyl-6,7-dihydro-5H-thiazolo-[3,2-a]pyrimidine-2-carboxamide hydrochloride.

Melting Point over 300° C.

Elementary Analysis for $C_{16}H_{15}N_3OSCl_2.HCl.0.3\ H_2O$ Calcd.: C,46.86 ; H,4.08 ; N,10.25. Found: C,46.86 ; H,3.68 ; N,9.71.

EXAMPLE 5

N-(4-Octylphenyl)-3-cyclopropyl-6,7-dihydro-5H-thiazolo[-3,2-a]pyrimidine-2-carboxamide hydrochloride Melting Point 263°–267° C.

Elementary Analysis for $C_{24}H_{33}N_3OS.HCl$ Calcd.: C,64.34; H,7.65; N,9.38. Found: C,63.96; H,7.47; N,9.25.

EXAMPLE 6

N-(3,5-Dimethoxyethyl)-3-cyclopropyl-6,7-dihydro-5H-thiazolo[3,2-a]pyrimidine-2-carboxamide hydrochloride Melting Point over 300° C. (decomposition)

Elementary Analysis for $C_{18}H_{21}N_3O_3S.HCl$ Calcd.: C,54.61; H,5.60; N,10.61. Found : C,54.36; H,5.60; N,10.72.

EXAMPLE 7

N-(4-Decylphenyl)-3-cyclobutyl-6,7-dihydro-5H-thiazolo[3,2-a]pyrimidine-2-carboxamide hydrochloride Melting Point 273°–277° C.

Elementary Analysis for $C_{27}H_{31}N_3OS.HCl$ Calcd.: C,66.16; H,8.23; N,8.57. Found: C,66.03; H,8.46; N,8.95.

EXAMPLE 8

N-(4-Octylphenyl)-3-cyclobutyl-6,7-dihydro-5H-thiazolo[3,2-a]pyrimidine-2-carboxamide hydrochloride Melting Point 280°–285° C.

Elementary Analysis for $C_{25}H_{35}N_3OS.HCl$ Calcd.: C,64.98; H,7.86; N,9.09. Found: C,64.97; H,7.67; N,9.34.

EXAMPLE 9

N-(3,5-Dichlorophenyl)-3-cyclopentyl-6,7-dihydro-5H-thiazolo[3,2-a]pyrimidine-2-carboxamide hydrochloride Melting Point 280°–285° C.

Elementary Analysis for $C_{18}H_{19}Cl_2N_3OS.HCl$ Calcd.: C,49.95; H,4.66; N,9.71. Found: C,50.13; H,4.59; N,9.47.

EXAMPLE 10

N-(3,5-Dichlorophenyl)-3-phenyl-6,7-dihydro-5H-thiazolo[3,2a-]pyrimidine-2-carboxamide hydrochloride Melting Point over 300° C.

Elementary Analysis for $C_{19}H_{15}N_3OSCl_2.HCl.0.5\ H_2O$ Calcd.: C,50.73; H,3.81; N,9.34. Found : C,50.87; H,3.88; N,9.34.

EXAMPLE 11

Ethyl 3-propyl-6,7-dihydro-5H-thiazolo[3,2-a]-pyrimidine-2-carboxylate hydrochloride

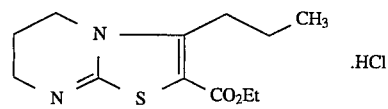

In 50 ml of anhydrous diethylether was dissolved 10 ml of ethyl butyryl acetate. To the solution was added dropwise 6 ml of sulfuryl chloride under cooling with ice. The temperature of the reaction mixture was raised slowly to room temperature, followed by stirring for 90 minutes. The reaction mixture was added in saturated sodium hydrogen carbonate aqueous solution and an organic layer was separated. The organic layer was washed with water, dried over anhydrous magnesium sulfate and consentrated. The oily residue was used in the next step without purification. 12.1 g of the residue was dissolved in 200 ml of methylethylketone. To the solution was added 5 g of 3,4,5,6-tetrahydro-2-pyrimidinethiol, followed by reflux under heating for 12 hours. After cooling the reaction mixture, the precipitated crystals were collected by filtration and washed with acetone to yield 13 g of the titled compound.

Melting Point 189°–191° C. $^1$H-NMR(D$_2$O) δ (ppm): 1.04(3H, t), 1.40(3H, t), 1.68(2H, q), 2.28(2H, t), 3.08, 3.64, 4.20(each 2H, t), 3.40(2H, q).

Elementary Analysis for C$_{12}$H$_{18}$N$_2$O$_2$S.HCl.0.2 H$_2$O Calcd.: C,48.95; H,6.64; N,9.52. Found : C,48.97; H,6.57; N,9.77.

EXAMPLE 12

3-Propyl-6,7-dihydro-5H-thiazolo[3,2-a]pyrimidine-2-carboxylic acid hydrochloride

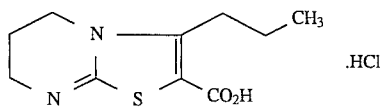

In 110 ml of 1N sodium hydroxide aqueous solution was suspended 9.96 g of ethyl 3-propyl-6,7-dihydro-5H-thiazolo[3,2-a]pyrimidine-2-carboxylate hydrochloride obtained in Example 11, followed by reflux under heating for 90 minutes. After cooling, the reaction mixture was made acidic with concentrated hydrochloric acid. The precipitated crystals were collected by filtration and washed with acetone to obtain 5.3 g of the titled compound.

Melting Point 225°–227° C. $^1$H-NMR(D$_2$O) δ (ppm): 1.10(3H, t), 1.74(2H, q), 2.34(2H, t), 3.16(2H, t), 3.72, 4.24(each 2H, t).

Elementary Analysis for C$_{10}$H$_{14}$N$_2$O$_2$S.HCl Calcd.: C,45.71; H,5.75; N,10.66. Found : C,45.76; H,5.76; N,10.64.

EXAMPLE 13

N-(3,5-dichlorophenyl)-3-propyl-6,7-dihydro-5H-thiazolo[3,2a-]pyrimidine-2-carboxamide hydrochloride

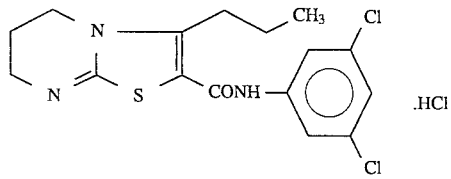

In 35 ml of thionyl chloride was suspended 5.3 g of 3-propyl-6,7-dihydro-5H-thiazolo[3,2-a]pyrimidine-2-carboxylic acid hydrochloride obtained Example 12, followed by reflux under heating for 40 minutes. The reaction mixture was cooled with ice, and poured into dry diethyl ether. The precipitated crystals were collected by filtration to yield 5.78 g of 3-propyl-6,7-dihydro-5H-thiazolo[3,2-a]pyrimidine-2-carbonyl chloride hydrochloride as colorless powder. This powder was suspended in the mixture of 200 ml of pyridine and 20 ml of dimethylformamide. To the mixture were added 3.38 g of 3.5-dichloroaniline and 250 mg of 3,5-dimethyl-aminopyridine, followed by stirring at 60° C. for 18 hours. The reaction mixture was concentrated and to the mixture was added water. The precipitated crystals were collected by filtration, washed successively with water and cold methanol and suspended in ethanol. To the mixture was added saturated hydrogenchloride diethylether. The formed crystals were collected by filtration and recrystallized from ethanol to obtain 3.65 g of the titled compound.

Melting Point 269°–272° C. $^1$H-NMR(D$_2$O) δ (ppm): 1.00(3H, t), 1.68(2H, q), 2.28(2H, t), 3.00(2H, t), 3.68, 4.20(each 2H, t), 7.40–7.65(3H, m).

Elementary Analysis for C$_{16}$H$_{17}$N$_3$OSCl$_2$.HCl Calcd.: C,47.24; H,4.46; N,10.33. Found: C,47.22; H,4.51; N,10.17.

The following compounds of Example 14 to 25 were prepared in a similar manner as described in Example 11 to 13.

EXAMPLE 14

N-(3,5-Dimethoxyphenyl)-3-propyl-6,7-dihydro-5H-thiazolo[3,2a-]pyrimidine-2-carboxamide hydrochloride Melting Point 262°–265° C.

Elementary Analysis for C$_{18}$H$_{23}$N$_3$O$_3$S.HCl Calcd.: C,54.33; H,6.08; N,10.56. Found : C,54.30; H,6.10; N,10.58.

EXAMPLE 15

N-(4-Nitorophenyl)-3-propyl-6,7-dihydro-5H-thiazolo[3,2-a]-pyrimidine-2-carboxamide hydrochloride Melting Point 278°–282° C.

Elementary Analysis for C$_{16}$H$_{18}$N$_4$O$_3$S.HCl Calcd.: C,50.19; H,5.00; N,14.63. Found: C,50.05; H,4.85; N,14.14.

EXAMPLE 16

N-(4-tert-Butylphenyl)-3-propyl-6,7-dihydro-5H-thiazolo[3,2-a]pyrimidine-2-carboxamide hydrochloride Melting Point 267°–270° C.

Elementary Analysis for C$_{20}$H$_{27}$N$_3$OS.HCl Calcd.: C,60.97; H,7.16; N,10.67. Found : C,60.84; H,7.21; N,10.73.

EXAMPLE 17

N-(4-Methoxyphenyl)-3-propyl-6,7-dihydro-5H-thiazolo[3,2-a]-pyrimidine-2-carboxamide hydrochloride Melting Point 251°–252° C.

Elementary Analysis for C$_{17}$H$_{21}$N$_3$O$_2$S.HCl.⅔ H$_2$O Calcd.: C,53.75; H,6.19; N,11.06. Found: C,53.73; H,6.09; N,10.78.

EXAMPLE 18

N-(2-Methoxyphenyl)-3-propyl-6,7-dihydro-5H-thiazolo[3,2-a]-pyrimidine-2-carboxamide hydrochloride Melting Point 266°–270° C.

Elementary Analysis for C$_{17}$H$_{21}$N$_3$O$_2$S.HCl0.52 H$_2$O Calcd.: C,54.18; H,6.15; N,11.15. Found: C,54.48; H,6.12; N,11.02.

EXAMPLE 19

N-(4-n-Octylphenyl)-3-propyl-6,7-dihydro-5H-thiazolo[3,2-a]-pyrimidine-2-carboxamide hydrochloride Melting Point 243°–245° C.

Elementary Analysis for $C_{24}H_{35}N_3OS.HCl$ Calcd.: C,64.05; H,8.06; N,9.34. Found: C,63.98; H,7.98; N,9.27.

EXAMPLE 20

N-(2,5-Dichloro-4-sulfophenyl)-3-propyl-6,7-dihydro-5H-thiazolo[3,2-a]pyrimidine-2-carboxamide hydrochloride Melting Point over 300° C.

Elementary Analysis for $C_{16}H_{16}Cl_2N_3NaO_4S_2.HCl.\frac{2}{5}H_2O$ Calcd.: C,40.07; H,3.53; N,8.76. Found: C,40.18; H,4.03; N,8.49.

EXAMPLE 21

N-(4-Decylphenyl)-3-propyl-6,7-dihydro-5H-thiazolo-[3,2-a]-pyrimidine-2-carboxamide hydrochloride Melting Point 239°–240° C.

Elementary Analysis for $C_{26}H_{39}N_3OS.HCl$ Calcd.: C,65.31; H,8.43; N,8.79. Found: C,65.36; H,8.48; N,8.74.

EXAMPLE 22

N-(4-Butylphenyl)-3-propyl-6,7-dihydro-5H-thiazolo-[3,2-a]-pyrimidine-2-carboxamide hydrochloride Melting Point 270°–277° C. (decomposition)

Elementary Analysis for $C_{20}H_{27}N_3OS.HCl$ Calcd.: C,60.97; H,7.16; N,10.67. Found: C,60.69; H,7.10; N,10.63.

EXAMPLE 23

N-(4-Hexylphenyl)-3-propyl-6,7-dihydro-5H-thiazolo-[3,2-a]-pyrimidine-2-carboxamide hydrochloride Melting Point 244°–252° C.

Elementary Analysis for $C_{22}H_{31}N_3OS.HCl$ Calcd.: C,62.61; H,7.64; N,9.96. Found: C,62.26; H,7.54; N,10.23.

EXAMPLE 24

N-(4-Propylphenyl)-3-propyl-6,7-dihydro-5H-thiazolo-[3,2-a]-pyrimidine-2-carboxamide hydrochloride Melting Point 276°–280° C.

Elementary Analysis for $C_{19}H_{25}N_3OS.HCl.0.25\ H_2O$ Calcd.: C,59.36; H,6.95; N,10.93. Found: C,59.53; H,7.20; N,10.91.

EXAMPLE 25

N-Phenyl-3-propyl-6,7-dihydro-5H-thiazolo[3,2-a]-pyrimidine-2-carboxamide hydrochloride Melting Point 253°–257° C.

Elementary Analysis for $C_{16}H_{19}N_3OS.HCl$ Calcd.: C, 56.88; H, 5.97; N, 12.44. Found: C,56.88; H,5.90; N,12.10.

EXAMPLE 26 tert-Butyl 3-methyl-6,7-dihydro-5H-thiazolo[3,2-a]pyrimidine-2-carboxylate hydrochloride

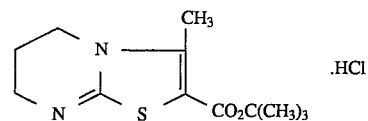

In 300 ml of anhydrous diethylether was dissolved 31.6 g of tert-butylacetyl acetate and to the mixture was added dropwise 17.6 ml of sulfuryl chloride under cooling with ice. After stirring at room temperature for 30 minutes, the reaction mixture was added to the ice-cooled 5% sodium hydrogen-carbonate aqueous solution and an organic layer was washed with water. The organic layer was separated, dreid over anhydrous magnesium sulfate and the solvent was removed under reduced pressure to yield 37.8 g as an oily residue. This residue was dissolved in 500 ml of methyl-ethylketone and to the solution was added 18.2 g of 3,4,5,6-tetrahydro-2-pyrimidinethiol, followed by reflux under heating for 12 hours. After cooling the reaction mixture, the precipitated crystals were collected by filtration. The crystals were washed successively with diethylether and acetone and suspended in 300 ml of isopropylalcohol. The suspension was refluxed under heating for 12 hours. The solvent was removed under reduced pressure. To the residue was added diethylether and the precipitated crystals were collected by filtration. The crystals were washed with acetone to yield 43.6 g of the titled compound.

Melting Point 232°–233° C. $^1$H-NMR ($D_2O$) δ (ppm): 1.60(9H, s), 2.24(2H, t), 2.60(3H, s), 3.64, 4.12(each 2H, t).

EXAMPLE 27

3-Methyl-6,7-dihydro-5H-thiazolo[3,2-a]pyrimidine-2-carboxylic acid hydrochloride

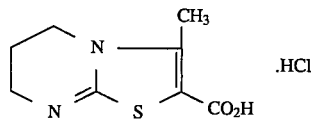

In 400 ml of 2N hydrochloric acid was suspended tert-butyl 3-methyl-6,7-dihydro-5H-thiazolo[3,2-a]-pyrimidine-2-carboxylate hydrochloride obtained in Example 26, followed by stirring at room temperature for 18 hours. The precipitated crystals were collected by filtration and washed successively with diethylether and acetone to yield 27.5 g of the titled compound.

Melting Point 237°–239° C. $^1$H-NMR($D_2O$) δ (ppm): 2.28(2H, t), 2.64(3H, s), 3.64, 4.12(each 2H, t).

EXAMPLE 28

N-(3,5-Dimethylphenyl)-3-methyl-6,7-dihydro-5H-thiazolo[3,2a-]pyrimidine-2-carboxamide hydrochloride

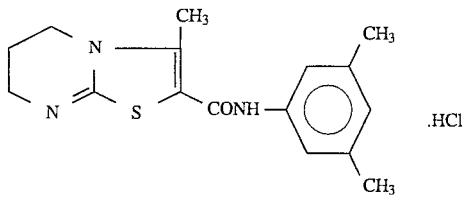

In 75 ml of thionylchloride was suspended 10.0 g of 3-methyl-6,7-dihydro-5H-thiazolo[3,2-a]pyrimidine-2-carboxylic acid hydrochloride obtained in Example 27, followed by reflux under heating for 30 minutes. After dissolving completely, the reaction mixture was cooled. To the reaction mixture was added anhydrous diethylether under cooling with ice. The formed crystals were collected by filtration and dried over under reduced pressure to yield 10.7 g of 3-methyl-6,7-dihydro-5H-thiazolo[3,2-a]pyrimidine-2-carbonylchloridehydrochloride. In 5 ml of pyridine were dissolved 490 mg of this crystal and 0.2 ml of 3,5-dimethylaniline, followed by stirring at room temperature for 6 hours. The reaction mixture was concentrated and to the concentrate was added 5% sodium hydrogencarbonate aqueous solution. The precipitated crystals were collected by filtration and washed with diethylether. The resulting powder was suspended in diethylether. To the suspension was added 0.5 ml of saturated hydrogenchloride aqueous solution, followed by stirring at room temperature. The precipitated crystals were collected by filtration. The crystals were recrystallized from ethanol to obtain 216 mg of the titled compound.

Melting Point 312°–316° C. $^1$H-NMR($D_2O$) δ (ppm): 2.28(2H, t), 2.38(6H, s), 2.56(3H, s), 3.64, 4.12(each 2H, t), 7.00–7.40(3H, m).

Elementary Analysis for $C_{16}H_{19}N_3OS.HCl.0.7\ H_2O$ Calcd.: C,54.83; H,6.15; N,11.99. Found: C,54.70; H,5.84; N,11.89.

The following compound of Example 29 to 35 were prepared in a similar manner as described in Example 26 to 28.

EXAMPLE 29

N-(4-Butylphenyl)-3-methyl-6,7-dihydro-5H-thiazolo-[3,2-a]-pyrimidine-2-carboxamide hydrochloride Melting Point 244°–251° C.

Elementary Analysis for $C_{18}H_{23}N_3OS.HCl.1.2\ H_2O$ Calcd.: C,55.79; H,6.87; N,10.84. Found: C,55.79; H,6.60; N,11.06.

EXAMPLE 30

N-(4-Methylphenyl)-3-methyl-6,7-dihydro-5H-thiazolo-[3,2-a]-pyrimidine-2-carboxamide hydrochloride Melting Point 256°–261° C.

Elementary Analysis for $C_{15}H_{17}N_3OS.HCl.1.5\ H_2O$ Calcd.: C,51.35; H,6.03; N,11.98. Found: C,51.90; H,5.68; N,11.73.

EXAMPLE 31

N-(4-Ethylphenyl)-3-methyl-6,7-dihydro-5H-thiazolo-[3,2-a]-pyrimidine-2-carboxamide hydrochloride Melting Point 228°–233° C.

Elementary Analysis for $C_{16}H_{19}N_3OS.HCl.H_2O$ Calcd.: C,54.00; H,6.18; N,11.81. Found: C,54.03; H,6.32; N,11.23.

EXAMPLE 32

N-(4-n-Propylphenyl)-3-methyl-6,7-dihydro-5H-thiazolo[3,2-a]-pyrimidine-2-carboxamide hydrochloride Melting Point 228°–233° C.

Elementary Analysis for $C_{17}H_{21}N_3OS.HCl.1.25\ H_2O$ Calcd.: C,54.53; H,6.60; N,11.22. Found: C,54.51; H,6.60; N,11.02.

EXAMPLE 33

N-(3,5-Difluorophenyl)-3-methyl-6,7-dihydro-5H-thiazolo[3,2a-]pyrimidine-2-carboxamide hydrochloride Melting Point 312°–318° C.

Elementary Analysis for $C_{14}H_{13}N_3OSF_2.HCl$ Calcd.: C,48.62; H,4.08; N,12.15. Found: C,48.76; H,3.99; N,11.85.

EXAMPLE 34

N-(4-Chlorophenyl)-3-methyl-6,7-dihydro-5H-thiazolo[3,2-a]-pyrimidine-2-carboxamide hydrochloride Melting Point 275°–278° C.

Elementary Analysis for $C_{14}H_{14}N_3OSCl.HCl.0.5\ H_2O$ Calcd.: C,47.66; H,4.57; N,11.91. Found: C,47.80; H,4.58; N,11.94.

EXAMPLE 35

N-(4-Bromophenyl)-3-methyl-6,7-dihydro-5H-thiazolo-[3,2-a]-pyrimidine-2-carboxamide hydrochloride Melting Point 289°–292° C.

Elementary Analysis for $C_{14}H_{14}N_3OSBr.HCl$ Calcd.: C,43.26; H,3.89; N,10.81. Found: C,43.24; H,3.99 ; N,10.81.

EXAMPLE 36

3-Pentyl-6,7-dihydro-5H-thiazolo[3,2-a]pyrimidine-2-carboxylic acid hydrochloride

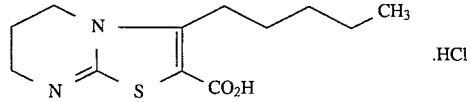

In 100 ml of anhydrous diethylether was dissolved 10.7 g of tert-butyl 3-oxononanoate obtained in Reference Example 2. To the solution was added dropwise 4.0 ml of sulfuryl chloride under cooling with ice, followed by stirring at room temperature for 45 minutes. The reaction mixture was added to ice-cooled saturated sodium hydrogencarbonate aqueous solution. The mixture was extracted with diethylether. The aqueous layer was made alkaline, dried over anhydrous magnesium sulfate. The solvent was removed under reduced pressure to yield 10.8 g of a colorless oily residue. The residue was dissolved in 250 ml of isopropylalcohol. To the mixture was added 4.3 g of 3,4,5,6-tetrahydro-2-pyrimidinethiol, followed by reflux under heating for 16 hours. To the reaction mixture was added 150 ml of saturated hydrogenchloride isopropylalcohol solution, followed by stirring at 80° C. for 4 hours. The reaction mixture was concentrated to 150 ml. After cooling, diethyether was added to the mixture and the precipitated crystals were collected by filtration. The crystals were washed successively with diethylether and acetone to yield 9.8 g of the titled compound.

Melting Point 212°–215° C. $^1$H-NMR(D$_2$O) δ (ppm): 0.73(3H, t), 0.99–1.45, 2.85(8H, t), 2.06(2H, t), 3.45, 3.95(each 2H, t).

EXAMPLE 37

N-(3,5-Dichlorophenyl)-3-pentyl-6,7-dihydro-5H-thiazolo[3,2a-]pyrimidine-2-carboxamide hydrochloride

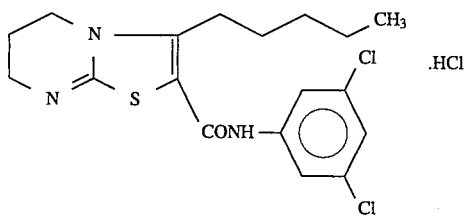

In 50 ml of thionylchloride was suspended 5.0 g of 3-pentyl-6,7-dihydro-5H-thiazolo[3,2-a]pyrimidine-2-carboxylic acid hydrochloride obtained in Example 36, followed by reflux under heating for 45 minutes. To the reaction mixture was added dropwise anhydrous diethylether her to crystallize under cooling. The crystals were collected by filtration, washed with anhydrous diethylether and dried under reduced pressure to obtain 5.2 g as a pale yellow crystal. In the mixture of 60 ml of pyridine and 10 ml of dimethylformamide was suspended 1.5 g of this crystals and to the mixture was added 790 mg of 3,5-dichloroaniline, followed by stirring at 60° C. for 24 hours. The solvent was removed under reduced pressure and to the residue was added water. The precipitated crystals were collected by filtration and washed successively with petroleum diethylether and cold methanol. The crystals were dissolved in methanol, followed by treating with active carbon. To the mixture was added saturated hydrogenchloride diethylether solution, followed by stirring at room temperature. The precipitated crystals were collected by filtration and washed with diethylether to yield 350 mg of the titled compound.

Melting Point 256°–260° C. $^1$H-NMR(D$_2$O) δ (ppm): 0.85(3H, t), 1.31–1.68(6H, m), 2.24(2H, t), 2.97(2H, t), 3.62, 4.16(each 2H, t), 7.40–7.50(3H, m).

Elementary Analysis for C$_{18}$H$_{22}$N$_3$OSCl$_2$.HCl Calcd.: C,49.71; H,5.10; N,9.65. Found: C,49.93; H,5.04; N,9.53.

The following compounds of Example 38 to 45 were prepared in a similar manner as described in Example 36 and 37.

EXAMPLE 38

N-(3,5-Dichlorophenyl)-3-butyl-6,7-dihydro-5H-thiazolo[3,2-a]pyrimidine-2-carboxamide hydrochloride Melting Point 248°–253° C.

Elementary Analysis for C$_{17}$H$_{19}$N$_3$O$_3$SCl$_2$.HCl Calcd.: C,48.52; H,4.79; N,9.99. Found: C,48.66; H,4.81; N,9.94.

EXAMPLE 39

N-(3,5-Difluorophenyl)-3-butyl-6,7-dihydro-5H-thiazolo[3,2-a]pyrimidine-2-carboxamide hydrochloride Melting Point 252°–257° C.

Elementary Analysis for C$_{17}$H$_{19}$N$_3$OSF$_2$.HCl Calcd.: C,52.64; H,5.20; N,10.83. Found: C,52.38; H,5.18; N,10.54.

EXAMPLE 40

N-(3,5-Difluorophenyl)-3-ethyl-6,7-dihydro-5H-thiazolo[3,2-a]pyrimidine-2-carboxamide hydrochloride Melting Point 280° C.

Elementary Analysis for C$_{15}$H$_{15}$N$_3$OSF$_2$.HCl Calcd.: C,50.07; H,4.48; N,11.68. Found: C,49.66; H,4.50; N,11.14.

EXAMPLE 41

N-(3,5-Dichlorophenyl)-3-ethyl-6,7-dihydro-5H-thiazolo[3,2-a]Pyrimidine-2-carboxamide hydrochloride Melting Point 270°–275° C.

Elementary Analysis for C$_{15}$H$_{15}$N$_3$O$_3$SCl$_2$.HCl Calcd.: C,45.87; H,4.10; N,10.70. Found: C,45.87; H,4.17; N,10.64.

EXAMPLE 42

N-(4-Octylphenyl)-3-ethyl-6,7-dihydro-5H-thiazolo-[3,2-a]-pyrimidine-2-carboxamide hydrochloride Melting Point 204°–206° C.

Elementary Analysis for C$_{23}$H$_{33}$N$_3$OS.HCl Calcd.: C,63.35; H,7.86; N,9.64. Found: C,62.95; H,8.19; N,9.75.

EXAMPLE 43

N-(4-Heptylphenyl)-3-ethyl-6,7-dihydro-5H-thiazolo-[3,2-a]-pyrimidine-2-carboxamide hydrochloride Melting Point 208°"209° C.

Elementary Analysis for C$_{22}$H$_{31}$N$_3$OS.HCl Calcd.: C,62.61; H,7.64; N,9.95. Found: C,62.27; H,7.94; N,9.93.

EXAMPLE 44

3-Tridesyl-6,7-dihydro-5H-thiazolo[3,2-a]pyrimidine-2-carboxylic acid hydrochloride Elementary Analysis for $C_{20}H_{34}N_2O_2S \cdot HCl$ Calcd.: C,59.60; H,8.75; N,6.95. Found: C,59.59; H,8.59; N,7.07.

EXAMPLE 45

N-(3,5-Dichlorophenyl)-3-tridecyl-6,7-dihydro-5H-thiazolo[3,2-a]pyrimidine-2-carboxamide hydrochloride Melting Point 124°"125° C.

EXAMPLE 46

3-Isopropyl-6,7-dihydro-5H-thiazolo[3,2-a]-pyrimidine-2-carboxylic acid hydrochloride

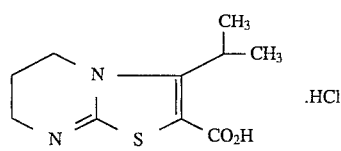

In 250 ml of dry diethylether was dissolved 20 g of tert-butyl 4-methyl-3-oxopentanoate obtained in Reference Example 3. To the solution was added dropwise 9.4 ml of sulfuryl chloride under cooling with ice, followed by stirring at the same temperature for 30 minutes. The reaction mixture was added to saturated sodium hydrogencarbonate aqueous solution. The organic layer was separated and washed with saturated sodium chloride aqueous solution and dried over anhydrous magnesium sulfate. The solvent was removed under reduced pressure. The residue was dissolved in 500 ml of isopropylalcohol and to the solution was added 10.8 g of 3,4,5,6-tetrahydro-2-pyrimidinethiol, followed by reflux under heating for 48 hours. To the reaction mixture was added to 100 ml of saturated hydrogenchloride dioxane solution, followed by reflux under heating for 12 hours. The mixture was concentrated. The precipitated crystals were collected by filtration and washed with diethylether to obtain 17.3 g of the titled compound.

Melting Point 213°"221° C. $^1$H-NMR($D_2O$) δ (ppm): 1.38(3H, s), 1.40(3H, s), 2.24(2H, m), 3.58(2H, t), 4.19(1H, m), 4.27(2H, t).

Elementary Analysis for $C_{10}H_{14}N_2O_2S \cdot HCl$ Calcd.: C,45.71; H,5.75; N,10.66. Found: C,45.75; H,5.73; N,10.66.

EXAMPLE 47

N-(2,5-Dimethoxyphenyl)-3-isopropyl-6,7-dihydro-5H-thiazolo[3,2-a]pyrimidine-2-carboxamide hydrochloride

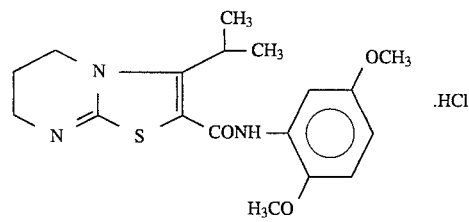

In 50 ml of thionylchloride was suspended 6.5 g of 3-isopropyl-6,7-dihydro-5H-thiazolo[3,2-a]pyrimidine-2-carboxylic acid hydrochloride obtained in Example 46, followed by reflux under heating for 1 hour. To the reaction mixture was added dry diethylether. The precipitated crystals were collected by filtration and washed with diethylether to obtain 7.0 g of 3-isopropyl-6,7-dihydro-5H-thiazolo[3,2-a]pyrimidine-2-carbonylchloride hydrochloride. In the mixture 5 ml of pyridine and 5 ml of dimethylformamide was dissolved 500 mg of this compound. To the solution was added 291 mg of 2,5-dimethoxyaniline, followed by stirring at 80üÅ for 12 hours. The solvent was removed under reduced pressure. The residue was crystallized from isopropylalcohol and diethylether. The resulting crystals were recrystallized from isopropylalcohol and saturated hydrogenchloride diethylether solution to obtain 200 mg of the titled compound.

Melting Point 235°"245° C. (decomposition) $^1$H-NMR($D_2O$) δ (ppm): 1.42(6H, d), 2.32(2H, m), 3.40(1H, m), 3.62(2H, m), 3.86(3H, s), 3.63(2H, m), 3.86(3H, s), 3.89(3H, s), 4.23(2H, m).

Elementary Analysis for $C_{18}H_{23}N_3O_3S \cdot HCl$ Calcd.: C,54.33; H,6.08; N,10.56. Found: C,54.24; H,6.14; N,10.52.

The following compounds of Example 48 to 51 were prepared in a similar manner as described in Example 46 and 47.

EXAMPLE 48

N-(3,5-Dichlorophenyl)-3-isopropyl-6,7-dihydro-5H-thiazolo[3,2-a]pyrimidine-2-carboxamide hydrochloride Melting Point 220°"226° C. $^1$H-NMR (CDCl$_3$) δ (ppm): 1.34(6H, d), 1.99(2H, q), 3.51(2H, t), 3.91(2H, t), 4.04(1H, s), 7.09(1H, t), 7.55(2H, q).

Elementary Analysis for $C_{16}H_{17}Cl_2N_3OS \cdot HCl$ Calcd.: C,51.90; H,4.63; N,11.35. Found: C,51.64; H,4.43; N,11.31.

EXAMPLE 49

N-(4-Methoxyphenyl)-3-isopropyl-6,7-dihydro-5H-thiazolo[3,2-a]pyrimidine-2-carboxamide hydrochloride Melting Point 255° C. $^1$H-NMR($D_2O$) δ (ppm): 1.40(6H, d), 2.22(2H, m), 3.39(1H, m), 3.58(2H, m), 3.90(3H, s), 4.18(2H, m), 3.39(1H, m), 3.58(2H, m), Elementary Analysis for $C_{17}H_{21}N_3O_2S \cdot HCl$ Calcd.: C,55.50; H,6.03; N,11.42. Found: C,55.45; H,5.95; N,11.31.

EXAMPLE 50

N-(2-Methoxyphenyl)-3-isopropyl-6,7-dihydro-5H-thiazolo[3,2-a]pyrimidine-2-carboxamide hydrochloride Melting Point 245°–255° C. (decomposition) $^1$H-NMR($D_2O$) δ (ppm): 1.38(6H, d), 2.24(2H, q), 3.45(2H, t), 3.58(2H, t), 3.89(3H, s), 4.19(9-H, t), 7.09(1H, t), 7.18(1H, d).

Elementary Analysis for $C_{17}H_{21}N_3O_2S \cdot HCl \cdot 0.7 H_2O$ Calcd.: C,53.66; H,6.20; N,11.04. Found: C,53.57; H,6.27; N,11.14.

EXAMPLE 51

N-(3,5-Dichlorophenyl)-3-isobutyl-6,7-dihydro-
5H-thiazolo-[3,2-a]pyrimidine-2-carboxamide
hydrochloride Melting Point 285° C. $^1$H-NMR(CDCl$_3$) δ (ppm): 0.76(6H, d), 1.75(1H, br), 2.06(2H, br), 2.68(2H, br), 3.43(2H, t), 3.97(2H, t), 7.22(1H, t), 7.30(2H, br).

Elementary Analysis for C$_{17}$H$_{19}$Cl$_2$N$_3$OS.HCl Calcd.: C,48.53; H,4.79; N,9.99. Found: C,48.39; H,4.80; N,9.84.

EXAMPLE 52

N-(3,5-Dichlorophenyl)-N-methyl-3-propyl-6,7-
dihydro-5H-thiazolo[3,2-a]pyrimidine-2-carboxamide
hydrochloride

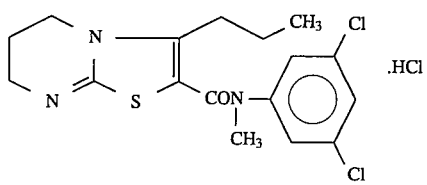

In the mixture of 30 ml of pyridine and 3 ml of dimethylformamide was suspended 938 mg of 3-propyl-6,7-dihydro-5H-thiazolo[3,2-a]pyrimidine-2-carbonylchloride hydrochloride (described in Example 13). To the suspension was added 587 mg of N-methyl-3,5-dichloroaniline, and 40 mg of dimethylaminopyridine, followed by stirring at 70° C. for 18 hours. The reaction mixture was cocentrated and to the mixture was added water. The organic layer was extracted with chloroform. The extact was washed with 5% sodium hydrogencarbonate aqueous solution and dried over anhydrous sodium sulfate. The solvent was removed under reduced pressure. The residue was dissolved in ethanol. To the solution was added saturated hydrogenchloride diethylether solution. The mixture was stirred at room temperature, followed by removing the solvent under reduced pressure. The residue was purified by column chromatography (silica gel: 45 g) using a mixed solvent of chloroform and methanol (20:1 by volume) as an eluent. The resulting substance was treated with saturated hydrogenchloride diethylether solution and recrystallized from a mixed solvent of ethanol and diethylether to obtain 461 mg of the titled compound.

Melting Point 228°"230° C. $^1$H-NMR(D$_2$O) δ (ppm): 0.80(3H, t), 1.37(2H, m), 1.97(2H, t), 2.53(2H, t), 3.24(3H, s), 3.34, 3.87 (each 2H, t), 7.25(2H, s), 7.26(1H, s).

Elementary Analysis for C$_{17}$H$_{19}$Cl$_2$N$_3$OS.HCl.0.5 H$_2$O Calcd.: C,47.51; H,4.92; N,9.78. Found: C,47.48; H,4.94; N,9.73.

The following compounds of Example 53 to 56 were prepared in a similar manner as described in Example 52.

EXAMPLE 53

N-(3,5-Dichlorophenyl)-N-methyl-3-cyclopropyl-6,7-
dihydro-5H-thiazolo[3,2-a]pyrimidine-2-carboxamide
hydrochloride Melting Point 275° C. $^1$H-NMR (D$_2$O) δ (ppm): 0.73(2H, br), 1.14(2H, br), 2.14(2H, br), 3.10(0.5H, s), 3.18(0.5H, s), 3.47(3H, s), 3.51(2H, br), 4.09(2H, br), 7.41(2H, d), 7.53(1H, br).

Elementary Analysis for C$_{17}$H$_{17}$Cl$_2$N$_3$OS.HCl.H$_2$O Calcd.: C,46.75; H,4.62; N,9.62. Found: C,46.87; H,4.67; N,9.76.

EXAMPLE 54

N-(3,5-Dichlorophenyl)-N-methyl-3-butyl-6,7-
dihydro-5H-thiazolo
[3,2-a]pyrimidine-2-carboxamide hydrochloride Melting Point 233°"236° C. $^1$H-NMR(D$_2$O) δ (ppm): 0.77(3H, t), 1.2–1.3(4H, m), 1.98(2H, ddd), 2.56(2H, t), 3.25(3H, s), 3.35, 3.88(each 2H, t), 7.25(2H, d), 7.38(1H, s).

Elementary Analysis for C$_{18}$H$_{21}$Cl$_2$N$_3$OS.HCl Calcd.: C,49.72; H,5.10; N,9.66. Found: C,49.50; H,5.12; N,9.55.

EXAMPLE 55

N-(3,5-Dichlorophenyl)-N-methyl-3-cyclohexyl-6,7-
dihydro-5H-thiazolo
[3,2-a]pyrimidine-2-carboxamide hydrochloride Melting Point 277°"283° C. $^1$H-NMR (DMSO-d$_6$) δ (ppm): 1.1–1.8(10H, m), 2.07(2H, m), 2.76(1H, m), 3.34(3H, s), 3.45, 4.04(each 2H, t), 7.58(3H, s).

Elementary Analysis for C$_{20}$H$_{23}$Cl$_2$N$_3$OS.HCl Calcd.: C,52.13; H,5.25; N,9.12. Found: C,52.21; H,5.22; N,8.88.

EXAMPLE 56

N-(3,5-Dichlorophenyl)-N-methyl-3-pentyl-6,7-
dihydro-5H-thiazolo[3,2-a]pyrimidine-2-carboxamide
hydrochloride Melting Point 241°"245° C.

Elementary Analysis for C$_{19}$H$_{23}$Cl$_2$N$_3$OS.HCl Calcd.: C,50.84; H,5.39; N,9.36. Found: C,50.85; H,5.58; N,9.19.

EXAMPLE 57

N-(3,5-Dichlorophenyl)-N-(2-ethoxycarbonylethyl)-
3-propyl-6,7-dihydro-5H-thiazolo[3,2-a]-
pyrimidine-2-carboxamide hydrochloride

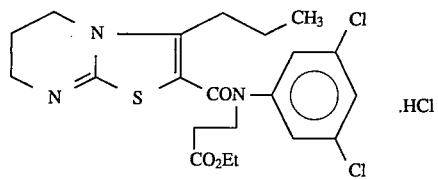

In the mixture of 30 ml of pyridine and 3 ml of dimethylformamide was suspended 1.09 g of 3-propyl-6,7-dihydro-5H-thiazolo[3,2-a]pyrimidine-2-carbonylchloride hydrochloride (described in Example 13). To the suspension was added 1.02 g of N-(2-ethoxycarbonylethyl)-3,5-dichloroaniline obtained in Reference Example 5 and 47.4 mg of 3,5-dimethylaminopyridine, followed by stirring at 70° C. for 20 hours. The reaction mixture was concentrated and to the mixture was added saturated sodium hydrogencarbonate aqueous solution. The organic layer was extracted with chloroform. The extact was washed with water and dried, followed by removing the solvent. The residue was dissolved in ethanol and to the solution was added saturated hydrogenchloride diethylether solution. The mixture was stirred at room temperature and the solvent was removed under reduced pressure. The residue was purified by column chromatography using a mixed solvent of chloroform and methanol (10:1 by volume) as an eluent. The resulting substance was crystallized from a mixed solvent of ethanol and diethylether. The formed crystals were recrystallized from a mixed solvent methanol and diethylether to obtain 109 mg of the titled compound.

Melting Point 149°"150° C. $^1$H-NMR(CDCl$_3$) δ (ppm): 1.08(3H, t), 1.25(3H, t), 1.64(2H, ddd), 2.17(2H, m), 2.59, 2.62(each 1H, d), 2.82(2H, m), 4.05(2H, t), 4.10(2H, q), 7.12(2H, m), 7.41(1H, t).

Elementary Analysis for $C_{21}H_{25}N_3O_3SCl_2 \cdot HCl0.25\ H_2O$ Calcd.: C,49.32; H,5.22; N,8.22. Found: C,48.94; H,4.75; N,8.32.

EXAMPLE 58

N-(3,5-Dichlorophenyl)-N-(2-carboxyethyl)-
3-propyl-6,7-dihydro-5H-thiazolo[3,2-a]-
pyrimidine-2-carboxamide hydrochloride

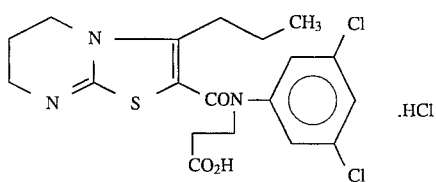

To 54.8 mg of N-(3,5-dichlorophenyl)-N-(2-ethoxycarbonylethyl)-3-propyl-6,7-dihydro-5H-thiazolo[3,2-a]-pyrimidine-2-carboxamide hydrochloride obtained in Example 57 was added 5 ml of concentrated hydrochloric acid, followed by stirring at 90° C. for 1 hour. After cooling, the solvent was removed under reduced pressure. The residue was suspended in isopropanol and to the suspension was added diethylether. The formed powder was collected by filtration. This powder was recrystallized from a mixed solvent of methanol and diethylether to obtain 41.9 mg of the titled compound.

Melting Point 224°"225° C. $^1$H-NMR(D$_2$O) δ (ppm): 0.83(3H, t), 1.40(2H, ddd), 1.97(2H, m), 2.51(2H, t), 2.56(2H, t), 3.33, 3.85(each 2H, t), 4.00(2H, t), 7.26(2H, d), 7.43(1H, t).

Elementary Analysis for $C_{19}H_{21}N_3O_3SCl_2 \cdot HCl \cdot 0.5\ H_2O$ Calcd.: C,46.78; H,4.75; N,8.61. Found: C,46.87; H,4.64; N,8.39.

The following compounds of Example 59 to 60 were prepared in a similar manner as described in Example 57 and 58.

EXAMPLE 59

N-(3,5-Dichlorophenyl)-N-(2-hydroxyethyl)-3-propyl-
6,7-dihydro-5H-thiazolo[3,2-a]pyrimidine-
2-carboxamide hydrochloride Melting Point 189°"190° C. $^1$H-NMR(DMSO-d$_6$) δ (ppm): 0.91(3H, t), 1.53(2H, ddd), 2.10(2H, m), 2.98(2H, t), 3.41(2H, q), 3.52, 4.08(each 2H, t), 4.37(2H, t), 6.53(1H, t), 6.60(2H, s).

Elementary Analysis for $C_{18}H_1N_3O_2SCl_2 \cdot HCl$ Calcd: C,47.96 H,4.91 ; N,9.32. Found: C,47.94 H,4.77 ; N,9.17.

EXAMPLE 60

N-(3,5-Dichlorophenyl)-N-(2-cyanoethyl)-3-propyl-
6,7-dihydro-5H-thiazolo[3,2-a]pyrimidine-
2-carboxamide hydrochloride Melting Point 202°–204° C. $^1$H-NMR(DMSO-d$_6$) δ (ppm): 0.97(3H, t), 1.48(2H, ddd), 2.03(2H, m), 2.78(2H, t), 2.83(2H, t), 3.44, 4.03(each 2H, t), 4.04(2H, t), 7.60(2H, d), 7.68(1H, Elementary Analysis for $C_{19}H_{20}N_4OSCl_2 \cdot HCl \cdot \frac{2}{3}\ H_2O$ Calcd.: C,48.37; H,4.77; N,11.87. Found: C,48.16; H,4.60; N,11.38.

EXAMPLE 61

3-Methyl-N-(2-pyridyl)-6,7-dihydro-5H-thiazolo-
[3,2-a]pyrimidine-2-carboxamide dihydrochloride

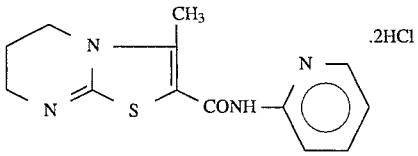

In 20 ml of pyridine was dissolved 200 mg of 3-aminopyridine. To this solution were added 50 mg of dimethylaminopyridine and 600 mg of 3-methyl-6,7-dihydro-5H-thiazolo[3,2-a]pyrimidine-2-carbonylchloride hydrochloride obtained in Example 28, followed by stirring at room temperature for 20 hours. The reaction mixture was concentrated and to the mixture was added saturated sodium hydrogencarbonate aqueous solution. The mixture was extracted with chloroform. The extact was washed with water and dried over anhydrous sodium sulfate. The solvent was removed under reduced pressure. The residue was dissolved in ethanol. To the solution was added saturated hydrogenchloride diethylether solution. The formed crystals were collected by filtration. This crystals were recrystallized from a mixed solvent of ethanol and diethylether to obtain 300 mg of the titled compound.

Melting Point 245°"249° C. $^1$H-NMR(D$_2$O) δ (ppm): 2.28(2H, t), 2.62(3H, s), 3.67, 4.18(each 2H, t), 7.48–8.60(4H, m).

Elementary Analysis for $C_{13}H_{14}N_4OS \cdot 2HCl \cdot 0.25\ H_2O$ Calcd.: C,44.39; H,4.73; N,15.93. Found: C,44.13; H,4.87; N,15.94.

The following compounds of Example 62 to 72 were prepared in a similar manner as described in Example 61.

EXAMPLE 62

3-Methyl-N-(3-pyridyl)-6,7-dihydro-5H-thiazolo-
[3,2-a]pyrimidine-2-carboxamide dihydrochloride Melting Point 246°"251° C. $^1$H-NMR(D$_2$O) δ (ppm): 2.24(2H, t), 2.58(3H, s), 3.64, 4.14(each 2H, t), 8.00–9.36(4H, m).

Elementary Analysis for $C_{13}H_{14}N_4OS \cdot 2HCl \cdot H_2O$ Calcd.: C,42.74; H,4.97; N,15.34. Found: C,42.84; H,4.90; N,15.34.

EXAMPLE 63

3-Methyl-N-[2-(1-piperidyl)ethyl]-6,7-dihydro-5H-thiazolo[3,2-a]pyrimidine-2-carboxamide dihydrochloride Melting Point 257°~261° C. $^1$H-NMR(D$_2$O) δ (ppm): 1.40–2.08(6H, br), 2.24(2H, t), 2.50(3H, s), 2.80–3,88, 4.10(each 10H, 2H, m).

Elementary Analysis for C$_{15}$H$_{24}$N$_4$OS.2HCl.¾H$_2$O Calcd.: C,45.62; H,7.02; N,14.19. Found: C,45.77; H,7.24; N,13.87.

EXAMPLE 64

3-Methyl-N-[2-(2-pyridyl)etyl]-6,7-dihydro-5H-thiazolo[3,2a-]pyrimidine-2-carboxamide dihydrochloride Melting Point 254°~258° C. $^1$H-NMR(D$_2$O) δ (ppm): 2.24(2H, t), 2.42(3H, s), 3.40, 3.62, 3.84, 4.08(each 2H, t).

Elementary Analysis for C$_{15}$H$_{18}$N$_4$OS.2HCl¾ H$_2$O Calcd.: C,46.27; H,5.57; N,14.39. Found: C,46.48; H,5.55; N,13.98.

EXAMPLE 65

3-Methyl-N-(2-pyrolidylethyl)-6,7-dihydro-5H-thiazolo[3,2-a]-pyrimidine-2-carboxamide dihydrochloride Melting Point 168°~173° C. $^1$H-NMR(D$_2$O) δ (ppm): 1.68–2.20(6H, m), 2.50(3H, s), 2.80–3.90, 4.10(each 2H, t).

Elementary Analysis for C$_{14}$H$_{22}$N$_4$OS.2HCl.1.2 H$_2$O Calcd.: C,43.23; H,6.84; N,14.40. Found: C,46.13; H,6.94; N,14.07.

EXAMPLE 66

3-Methyl-N-(2-morpholinoethyl)-6,7-dihydro-5H-thiazolo[3,2-a]pyrimidine-2-carboxamide dihydrochloride Melting Point 248°~253° C. $^1$H-NMR(D$_2$O) δ (ppm): 2.20(2H, t), 2.48(3H, s), 3.00–4.20(16H, m).

Elementary Analysis for C$_{14}$H$_{22}$N$_4$OS.2HCl.0.5 H$_2$O Calcd.: C,42.85; H,6.42; N,14.28. Found: C,42.87; H,6.50; N,14.30.

EXAMPLE 67

3-Methyl-N-(2-thiazolyl)-6,7-dihydro-5H-thiazolo[3,2-a]pyrimidine-2-carboxamide hydrochloride Melting Point 280°~293° C. (composition)

Elementary Analysis for C$_{11}$H$_{12}$N$_4$OS.HCl Calcd.: C,41.70; H,4.14; N,17.69. Found: C,41.67; H,4.14; N,17.68.

EXAMPLE 68

3-Methyl-N-[2-(1,3,4-thiadiazolyl)]-6,7-dihydro-5H-thiazolo[3,2-a]pyrimidine-2-carboxamide hydrochloride Melting Point 295°~298° C.

Elementary Analysis for C$_{10}$H$_{11}$N$_5$OS$_2$.HCl Calcd.: C,37.79; H,3.81; N,22.04. Found: C,37.78; H,3.90; N,21.57.

EXAMPLE 69

N-(2-Benzothiazolyl)-3-methyl-6,7-dihydro-5H-thiazolo[3,2-a]pyrimidine-2-carboxamide hydrochloride Melting Point over 300° C.

Elementary Analysis for C$_{15}$H$_{14}$N$_4$OS$_2$.HCl Calcd.: C,49.10; H,4.12; N,15.27. Found: C,48.96; H,4.15; N,15.31.

EXAMPLE 70

N-[2-(5-Chlorobenzoxazolyl)]-3-methyl-6,7-dihydro-5H-thiazolo[3,2-a]pyrimidine-2-carboxamide hydrochloride Melting Point 297°~298° C.

Elementary Analysis for C$_{15}$H$_{13}$N$_4$OS$_2$Cl.HCl Calcd.: C,46.76; H,3.66; N,14.54. Found: C,46.60; H,3.71; N,14.50.

EXAMPLE 71

N-(cis-9-Octyldecenyl)-3-propyl-6,7-dihydro-5H-thiazolo[3,2-a]pyrimidine-2-carboxamide hydrochloride

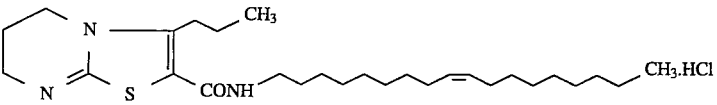

In the mixture of 30 ml of pyridine and 3 ml of dimethylformamide was suspended 849 mg of 3-propyl-6,7-dihydro-5H-thiazolo[3,2-a]pyrimidine-2-carbonylchloride hydrochloride (described in Example 13). To the suspension were added 807 mg of oleyl amine and 36 mg of 3,5-dimethylaminopyridine, followed by stirring at 70° C. for 20 hours. The reaction mixture was concentrated and to the concentrate was added saturated sodium hydrogencarbonate aqueous solution. The mixture was extracted with chloroform. The extract was washed with saturated sodium chloride aqueous solution, dried over anhydrous sodium sulfate and treated with active carbon. The solvent was removed under reduced pressure. The residue was dissolved in ethanol and to the solution was added saturated hydrogenchloride diethylether solution, followed by stirring at room temperature. After removing the solvent, the residue was purified by silica gel column chromatography (silica gel: 150 g) using a mixed solvent of chloroform and methanol (20:1 by volume). The purified substance was added to saturated hydrogenchloride diethylether solution, followed by stirring at room temperature. The solvent was removed under reduced pressure. The residue was crystallized from hexane-diethylether to obtain 203 mg of the titled compound.

Melting Point 133°~134° C. $^1$H-NMR(DMSO-d$_6$) δ (ppm): 0.88(3H, t), 1.03(3H, t), 1.25–1.30(22H, m), 1.55–1.65(3H, m), 1.93–2.0(5H, m), 2.23(2H, m), 2.99(2H, t), 3.31(2H, t), 3.68, 4.07(each 2H, t), 5.3–5.4(2H, m), 7.27(1H, brs).

Elementary Analysis for $C_{28}H_{49}N_3OS \cdot HCl \cdot 1.5\ H_2O$ Calcd.: C,62.36; H,9.91; N,7.79. Found: C,62.32; H,9.63; N,7.95.

The following compounds of Example 72 to 76 were prepared in a similar manner as described in Example 71.

EXAMPLE 72

N-(cis-9-Octyldecenyl)-3-methyl-6,7-dihydro-5H-thiazolo[3,2-a]pyrimidine-2-carboxamide Melting Point 91°"92° C. $^1$H-NMR(CDCl$_3$) δ (ppm): 0.88(3H, t), 1.1°"1.4(25H, m), 1.53(2H, ddd), 1.95–2.05(4H, m), 2.43(3H, s), 3.30(2H, q), 3.50, 3.71(each 2H, t), 5.3–5.4(2H, m).

Elementary Analysis for $C_{26}H_{45}N_3OS \cdot HCl \cdot 0.5\ H_2O$ Calcd.: C,68.37; H,10.15; N,9.20. Found: C,68.25; H,10.35; N,9.36.

EXAMPLE 73

N-(cis-9-Octyldecenyl)-3-cyclopropyl-6,7-dihydro-5H-thiazolo-[3,2-a]pyrimidine-2-carboxamide hydrochloride Melting Point 172°"178° C. $^1$H-NMR(CDCl$_3$) δ (ppm): 0.86(2H, d), 0.88(3H, t), 1.1–1.4(26H, m), 1.65(2H, m), 1.7–2.3(5H, m), 3.37(2H, m), 3.52, 4.24(each 2H, t), 5.3–5.4(2H, m), 7.27(1H, brs).

Elementary Analysis for $C_{28}H_{47}N_3OS \cdot HCl$ Calcd.: C,65.91; H,9.48; N,8.24. Found: C,65.49; H,9.74; N,8.27.

EXAMPLE 74

3-Methyl-N-n-octadecyl-6,7-dihydro-5H-thiazolo-[3,2-a]-pyrimidine-2-carboxamide hydrochloride Melting Point 124°"125° C.

Elementary Analysis for $C_{26}H_{47}N_3OS \cdot HCl$ Calcd.: C,64.22; H,9.95; N,8.64. Found: C,64.11; H,10.33; N,8.61.

EXAMPLE 75

3-Methyl-N-t-octyl-6,7-dihydro-5H-thiazolo[3,2-a]-pyrimidine-2-carboxamide hydrochloride Melting Point 230°"231° C.

Elementary Analysis for $C_{16}H_{27}N_3OS \cdot HCl$ Calcd.: C,55.55; H,8.16; N,12.15. Found: C,55.46; H,8.13; N,12.24.

EXAMPLE 76

3-Methyl-N-n-octyl-6,7-dihydro-5H-thiazolo[3,2-a]-pyrimidine-2-carboxamide hydrochloride Melting Point 134°"139° C.

Elementary Analysis for $C_{16}H_{27}N_3OS \cdot HCl$ Calcd.: C,55.55; H,8.16; N,12.15. Found: C,55.20; H,8.18; N,12.12.

EXAMPLE 77 t-Butyl 3-(2-ethoxycarbonylethyl)-6,7-dihydro-5H-thiazolo-[3,2-a]-pyrimidine-2-carboxylate hydrochloride

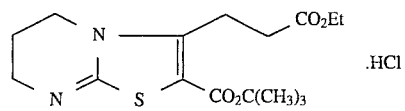

In 200 ml of dry diethylether was dissolved 13.0 g of tert-butyl 6-ethoxycarbonyl-3-oxopentanoate obtained in Reference Example 4. To the solution was added dropwise 4.28 ml of sulfurylchloride under cooling with ice. The reaction mixture was stirred at room temperature for 30 minutes and added to cold sodium hydrogencarbonate aqueous solution. The organic layer was washed with water and dried over anhydrous magnesium sulfate. The solvent was removed under reduced pressure. The residue was dissolved in 300 ml of isopropylalcohol and to the solution was added 5.22 g of 3,4,5,6-tetrahydro-2-pyrimidinethiol, followed by reflux under heating for 12 hours. After cooling the mixture, isopropylalcohol was removed under reduced pressure. To the residue was added diethylether to crystallize. The crystals were obtained 13.7 g of the titled compound.

$^1$H-NMR(CDCl$_3$) δ (ppm): 1.26(3H, t), 1.53(9H, s), 2.24(2H, m), 2.77(2H, t), 3.21(2H, t), 3.70, 4.24(each 2H, t).

EXAMPLE 78

3-(2-Ethoxycarbonylethyl)-6,7-dihydro-5H-thiazolo-[3,2-a]-pyrimidine-2-carboxylic acid hydrochloride

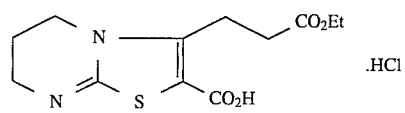

In saturated hydrogenchloride ethanol solution was suspended 13.4 g of tert-butyl 3-(2-ethoxycarbonylethyl)-6,7-dihydro-5H-thiazolo[3,2-a]pyrimidine-2-carboxylate hydrochloride obtained in Example 77, followed by stirring at room temperature for 18 hours. The precipitated crystals were collected by filtration and washed with diethylether to yield 5.63 g of the titled compound.

Melting Point 213°"216° C. $^1$H-NMR(D$_2$O) δ (ppm): 1.09(3H, t), 2.08(2H, m), 2.58(2H, m), 3.21(2H, t), 3.44, 3.99(each 2H, m). 4.01(2H, t).

Elementary Analysis for $C_{12}H_{16}N_2O_4S \cdot HCl$ Calcd.: C,44.93; H,5.34; N,8.73. Found: C,44.96; H,5.04; N,8.59.

EXAMPLE 79

N-(4-Octylphenyl)-3-(2-ethoxycarbonylethyl)-6,7-dihydro-5H-thiazolo[3,2-a]pyrimidine-2-carboxamide hydrochloride

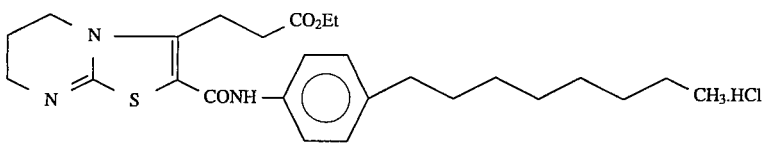

In 15 ml of thionylchloride was suspended 3.0 g of 3-(2-ethoxy- carbonylethyl)-6,7-dihydro-5H-thiazolo[3,2-a]-pyrimidine-2-carboxylic acid hydrochloride obtained in Example 78, followed by reflux under heating for 20 minutes. After cooling, dry diethylether was added to the mixture to crystallize. Diethylether was removed by decantation. The residue was washed with diethylether, followed by repeating decantation. After drying under reduced pressure, 3.26 g of precipitated crystals were suspended in the mixture of 80 ml of pyridine and 8 ml of dimethylformamide. To the suspension were added 1.92 g of 4-octylaniline and 114 mg of 3,5-dimethylaminopyridine, followed by stirring at 70° C. for 18 hours. After cooling, the reaction mixture was cocentrated and added to saturated sodium hydrogencarbonate aqueous solution, followed by extracting with chloroform. The extract was washed with saturated sodium chloride aqueous solution, dried over anhydrous potassium carbonate and treated with active carbon. The solvent was removed under reduced pressure. The residue was dissolved in ethanol and to the solution was added saturated hydrogenchloride diethylether solution, followed by stirring 1 hour. After removing solvent, the residue was purified by silica gel column chromatography using a mixed solvent of chloroform and methanol (10:1 by volume). To the resulting substance was added saturated hydrogenchloride diethylether solution. The mixture was recrystallized from methanoldiethylether to obtain 2.31 g of the titled compound.

Melting Point 225°"226° C. $^1$H-NMR(CDCl$_3$) δ (ppm): 0.88(3H, t), 1.25(3H, t), 1.20–1.35(10H, m), 1.57(2H, m), 2.25 (2H, m), 2.55(2H, t). 2.83(2H, m), 3.28(2H, t), 3.62, 4.23(each 2H, m), 4.14(2H, q), 7.10(2H, d), 7.52(2H, d).

Elementary Analysis for $C_{26}H_{37}N_3O_3S.HCl.0.5\ H_2O$ Calcd.: C,60.39; H,7.60; N,8.13. Found: C,60.38; H,7.34; N,8.15.

EXAMPLE 80

N-(4-Octylphenyl)-3-(2-carboxyethyl)-6,7-dihydro-5H-thiazolo-[3,2-a]pyrimidine-2-carboxamide hydrochloride

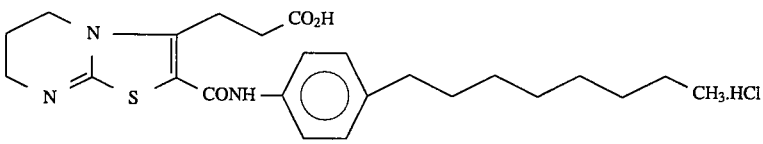

In 30 ml of ethanol was dissolved 720 mg of N-(4-octylphenyl)-3-(2-ethoxycarbonylethyl)-6,7-dihydro-5H-thiazolo[3,2-a]pyrimidine-2-carboxamide hydrochloride obtained in Example 79. To the solution was added 3.5 ml of 1N sodium hydroxide aqueous solution, followed by stirring at room temperature for 16 hours. The solvent was removed under reduced pressure. To the residue was added 1N hydrochloric acid to make acidic. The precipitated crystals were washed with diethylether to obtain 628 mg of the titled compound.

Melting Point 147°"153° C. $^1$H-NMR (DMSO-d$_6$) δ (ppm): 0.86(3H, t), 1.2–1.3(10H, m), 1.55(2H, m), 2.12(2H, m), 2.54(2H, t), 2.67(2H, t), 3.19(2H, t), 3.53, 4.13(each 2H, m), 7.15(2H, d), 7.52(2H, d), 10.50(1H, brs).

Elementary Analysis for $C_{24}H_{33}N_3O_3S.HCl$ Calcd.: C,60.05; H,7.14; N,8.75. Found: C,59.69; H,7.33; N,8.59.

The following compounds of Example 81 to 83 were prepared in a simila manner as described in Example 77 to 80.

EXAMPLE 81

N-(4-Octylphenyl)-3-(3-carboxypropyl)-6,7-dihydro-5H-thiazolo[3,2-a ]pyrimidine-2-carboxamide hydrochloride Melting Point 205°"206° C. $^1$H-NMR(DMSO-d$_6$) δ (ppm): 0.86(3H, t), 1.2–1.3(10H, m), 1.54(2H, m), 1.79(2H, m), 2.10(2H, m), 2.35(2H, t), 2.54(2H, t), 3.00(2H, t), 3.51, 4.10(each 2H, m), 7.14(2H, d), 7.50(2H, d), 1.57(1H, brs).

EXAMPLE 82

N-(4-Octylphenyl)-3-(2-cyanoethyl)-6,7-dihydro-5H-thiazolo-[3,2-a]pyrimidine-2-carboxamide hydrochloride Melting Point 136°–137° C. $^1$H-NMR(CDCl$_3$) δ (ppm): 0.88(3H, t), 1.2–1.35(10H, m), 1.5–1.6(3H, m), 2.01(9. H, m), 2.60(2H, t), 2.83(2H, t). 3.20(2H, t), 3.54, 3.87(each 2H, m), 7.15(2H, d), 7.34(2H, d).

EXAMPLE 83

N-(4-Octylphenyl)-3-(3-cyanopropyl)-6,7-dihydro-5H-thiazolo-[3,2-a]pyrimidine-2-carboxamide hydrochloride Melting Point 83°"84° $^1$H-NMR(CDCl$_3$) δ (ppm): 0.88(3H, t), 1.2–1.35(10H, m), 1.5–1.6(3H, m), 2.01(2H, m), 2.22(2H, t), 2.53(2H, t), 3.12(2H, t), 3.64, 4.11(each 2H, m), 7.07(2H, d), 7.56(2H, d).

EXAMPLE 84

N-(4-n-Heptylthiophenyl)-3-propyl-6,7-dihydro-5H-thiazolo-[3,2-a]pyrimidine-2-carboxamide hydrochloride

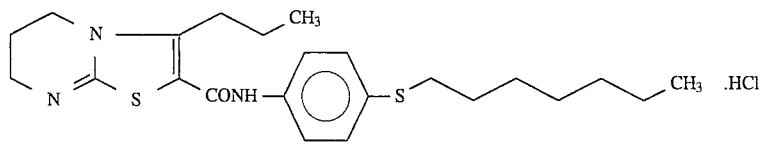

In the mixture of 50 ml of pyridine and 5 ml of dimethylformamide was suspended 1.07 g of 3-propyl-6,7-dihydro-5H-thiazolo[3,2-a]pyrimidine-2-carbonylchloride hydrochloride (described in Example 13). To the suspension were added 850 mg of 4-n-heptylthioaniline obtained in Reference Example 6, and 56 mg of 3,5-dimethylaminopyridine, followed by stirring at 70° C. for 12 hours. The reaction mixture was concentrated and to the concentrate was added saturated sodium hydrogencarbonate aqueous solution. The mixture was extracted with chloroform. The extract was washed with saturated sodium chloride aqueous solution, dried over anhydrous potassium carbonate and treated with active carbon. The solvent was removed under reduced pressure. The residue was dissolved in ethanol. To the mixture was added saturated hydrogenchloride diethylether solution, followed by stirring at room temperature. The solvent was removed under reduced pressure. The residue was precipitated from ethanol-diethylether to collect by filtration. The precipitated powder was recrystallized from methanoldiethylether to yield 992 mg of the titled compound.

Melting Point 206°"207° C. $^1$H-NMR(CDCl$_3$) δ (ppm): 0.88(3H, t), 1.00(3H, t), 1.2–1.35(4H, m), 1.35–1.45(2H, m), 1.55–1.7(6H, m), 2.15–2.22(2H, m), 2.87(2H, t), 2.98(2H, t), 3.56, 4.04(each 2H, t), 7.27(2H, d), 7.66(2H, d).

Elementary Analysis for C$_{23}$H$_{33}$N$_3$OS$_2$.HCl Calcd.: C,59.01; H,7.32; N,8.98. Found: C,58.95; H,7.36; N,9.26.

EXAMPLE 85

N-(4-n-Heptylsulfonylphenyl)-3-propyl-6,7-dihydro-5H-thiazolo[3,2-a]pyrimidine-2-carboxamide hydrochloride

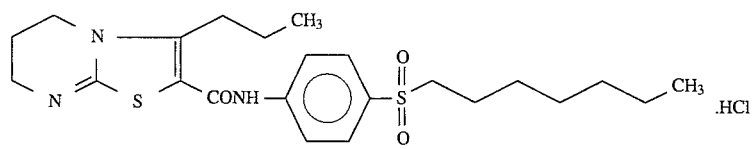

In the mixture of 50 ml of pyridine and 5 ml of dimethylformamide was suspended 1.04 g of 3-propyl-6,7-dihydro-5H-thiazolo[3,2-a]pyrimidine-2-carbonyl-chloridehydrochloride (described in Example 13). To the suspension was added 940 mg of 4-n-heptylsulfonylaniline obtained in Reference Example 7, and 45 mg of 3,5-dimethylaminopyridine, followed by stirring at 70° C. for 17 hours. The reaction mixture was concentrated and to the concentrate was added saturated sodium hydrogencarbonate aqueous solution. The mixture was extracted with chloroform. The extract was washed with saturated sodium chloride aqueous solution and dried over anhydrous potassium carbonate. The solvent was removed under reduced pressure. The residue was dissolved in ethanol. To the mixture was added saturated hydrogenchloride diethylether solution, followed by stirring at room temperature. The solvent was removed under reduced pressure. The residue was purified by silica gel column chromatography using a mixed solvent of chloroform and methanol (10:1 by volume). To the resulting substance was added saturated hydrogenchloride diethylether solution. The solvent was removed under reduced pressure. The residue was recrystallized from methanol-diethylether to obtain 559 mg of the titled compound.

Melting Point 231°"236° C. (decomposition) $^1$H-NMR(CDCl$_3$) δ (ppm): 0.86(3H, t), 1.02(3H, t), 1.2–1.4(8H, m), 1.55–1.7(4H, m), 2.15–2.25(2H, m), 2.76(1H, brs), 2.90(2H, t), 3.03(2H, t), 3.64, 4.05(each 2H, t), 7.77(2H, d), 8.11(2H, d).

Elementary Analysis for C$_{23}$H$_{33}$N$_3$O$_3$S$_2$.HCl Calcd.: C,55.24; H,6.85; N,8.40. Found: C,55.30; H,7.06; N,8.31.

The following compounds of Example 86 to 88 were prepared in a similar manner as described in Example 84 and 85.

EXAMPLE 86

N-[4-(2-n-Butoxyethylsulfonyl)phenyl]-3-propyl-6,7-dihydro-H-thiazolo[3,2-a]pyrimidine-2-carboxamide hydrochloride Melting Point 238°"245° C. $^1$H-NMR(DMSO-d$_6$) δ (ppm): 0.78(3H, t), 0.94(3H, t), 1.05–1.15(2H, m), 1.2–1.3(2H, m), 1.55–1.65(2H, m), 2.18–2.28(2H, m), 2.98(2H, t), 3.20, 3.54(each 2H, t), 3.55, 4.12 (each 2H, t), 3.64(2H, t), 7.85(2H, d), 7.90(2H, d).

Elementary Analysis for C$_{22}$H$_{31}$N$_3$O$_4$S$_2$.HCl Calcd.: C,52.63; H,6.42; N,8.37. Found: C,52.80; H,6.13; N,8.14.

EXAMPLE 87

N-[4-(2-n-Butoxyethoxy)phenyl]-3-propyl-6,7-dihydro-5H-thiazolo[3,2-a]pyrimidine-2-carboxamide hydrochloride Melting Point 208°"210° $^1$H-NMR(DMSO-d$_6$) δ (ppm): 0.88(3H, t), 0.93(3H, t), 1.28–1.38(2H, m), 1.45–1.55(2H, m), 1.52–1.62(2H, m), 2.12(2H, m), 2.97(2H, t), 3.45(2H, t), 3.53, 4.10(each 2H, t), 3.68(2H, t), 4.06(2H, t), 6.92(2H, d), 7.50(2H, d).

Elementary Analysis for C$_{22}$H$_{31}$N$_3$O$_3$S.HCl.⅓ H$_2$O Calcd.: C,57.44; H,7.16; N,9.13. Found: C,57.11; H,6.71; N,8.95.

EXAMPLE 88

N-(4-Heptyloxyphenyl)-3-propyl-6,7-dihydro-
5H-thiazolo[3,2-a]pyrimidine-2-carboxamide
hydrochloride Melting Point 239°–240° C. $^1$H-NMR(CDCl$_3$) δ (ppm): 0.90(3H, t), 0.98(3H, t), 1.2–1.4(6H, m), 1.4–1.5(2H, m), 1.55–1.65(2H, m), 1.7–1.8(2H, m), 2.02(1H, brs), 2.16(2H, m), 2.97(2H, t), 3.56, 4.06 (each 2H, t), 3.90(2H, t), 6.81(2H, d), 7.61(2H, d).

Elementary Analysis for $C_{23}H_{33}N_3O_2S \cdot HCl$ Calcd.: C,61.11; H,7.58; N,9.30. Found: C,60.87; H,7.56; N,9.40.

EXAMPLE 89

N-[4-(5-Ethoxycarbonylpentylthio)phenyl]-3-propyl-
6,7-dihydro-5H-thiazolo[3,2-a]pyrimidine-
2-carboxamide hydrochloride

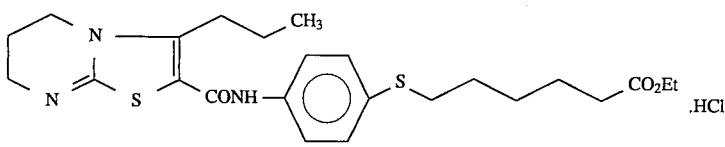

In the mixture of 50 ml of pyridine and 5 ml of dimethylformamide was suspended 0.95 g of 3-propyl-6,7-dihydro-5H-thiazolo[3,2-a]pyrimidine-2-carbonylchloride hydrochloride (described in Example 13). To the suspension was added 1.0 g of 4-(5-ethoxycarbonylpentylthio) aniline prepared in a similar manner as described in Reference Example 7 and added 43.4 mg of dimethylaminopyridine, followed by stirring at 70° C. for 16 hours. The reaction mixture was concentrated and to the concentrate was added saturated sodium hydrogencarbonate aqueous solution. The mixture was extracted with chloroform. The extract was washed with saturated sodium chloride aqueous solution and dried over anhydrous potassium carbonate. The solvent was removed under reduced pressure. The residue was dissolved in ethanol. To the mixture was added saturated hydrogenchloride diethylether solution and stirred at room temperature, following by removing the solvent under reduced pressure. The residue was purified by silica gel column chromatography (silica gel:100 g) using a mixed solvent of chloroform and methanol (10:1 by volume) as an eluent. To the resulting substance was added saturated hydrogenchloride diethylether solution. The solvent was removed under reduced pressure. The residue was recrystallized from methanol-diethylether to obtain 632 mg of the titled compound.

Melting Point 145°"147° C. $^1$H-NMR(CDCl$_3$) δ (ppm): 0.99(3H, t), 1.25(3H, t), 1.45(2H, m), 1.63(6H, m), 2.18(2H, m), 2.29(2H, t), 2.87(2H, t), 2.97(2H, t), 3.56, 4.04(each 2H, m), 4.12(2H, q), 7.26(2H, d), 7.69(2H, d), 9.86(1H, s, NH).

Elementary Analysis for $C_{24}H_{33}N_eO_3S_2 \cdot HCl$ Calcd.: C,56.29; H,6.69; N,8.20. Found: C,55.94; H,7.69; N,8.15.

EXAMPLE 90

N-[4-(5-Carboxypentylthio)phenyl]-3-propyl-6,7-
dihydro-5H-thiazolo[3,2-a]pyrimidine-2-carboxamide
hydrochloride

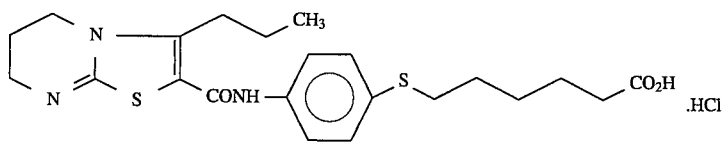

In 30 ml of ethanol was dissolved 750 mg of N-[4-(5-ethoxycarbonyl-pentylthio)phenyl]-3-propyl- 6,7-dihydro-5H-thiazolo[3,2-a]pyrimidine-2-carboxamide hydrochloride obtained in Example 89. To the solution was added 3.22 ml of 1N sodium hydroxide aqueous solution, followed by reflux under heating for 2 hours. After cooling the mixture, ethanol was removed under reduced pressure. The aqueous solution was made acidic with consentrated hydrochloric acid, following by removing a little amount of water. To the residue was added isopropylalcohol-diethylether and the precipitated crystals were collected by filtration. This crystals were recrystallized from methanol-diethylether to obtain 494 mg of the titled compound.

Melting Point 177°"180° C. $^1$H-NMR(CDCl$_3$) δ (ppm): 0.94(3H, t), 1.35–162(8H, m), 2.13(2H, m), 2.19(2H, t), 2.91(2H, t), 2.98(2H, m), 3.55, 4.11(each 2H, m), 7.31(2H, d), 7.64(2H, d).

Elementary Analysis for $C_{22}H_{29}N_3O_3S_2 \cdot HCl$ Calcd.: C,54.59; H,6.25; N,8.68. Found: C,54.37; H,5.93; N,8.53.

The following compounds of Example 91 to 104 were prepared in a similar manner as described in Example 89 and 90.

EXAMPLE 91

N-[4-(5-Ethoxycarbonylpentylthio)phenyl]-3-
methoxymethyl-6,7-dihydro-5H-thiazolo[3,2-a]-
pyrimidine-2-carboxamide hydrochloride Melting Point 128°"129° C.

Elementary Analysis for $C_{23}H_{31}N_3O_4S_2 \cdot HCl$ Calcd.: C,53.73; H,6.27; N,8.17. Found: C,53.35; H,6.14; N,7.88.

EXAMPLE 92

N-[4-(5-Carboxypentylthio)phenyl]-3-methoxymethyl-6,7-dihydro-5H-thiazolo[3,2-a]pyrimidine-2-carboxamide hydrochloride Melting Point 234°"235° C.

Elementary Analysis for $C_{21}H_{27}N_3O_4S_2 \cdot HCl$ Calcd.: C, 51.89; H, 5.81; N, 8.63. Found: C,52.24; H,5.81; N,8.63.

EXAMPLE 93

N-[4-(4-Etoxycarbonylbutylthio)phenyl]-3-methoxymethyl-6,7-dihydro-5H-thiazolo[3,2-a]-pyrimidine-2-carboxamide hydrochloride Melting Point 124°"125° C.

Elementary Analysis for $C_{22}H_{29}N_3O_4S_2 \cdot HCl$ Calcd.: C,52.84; H,6.05; N,8.40. Found: C,52.25; H,5.77; N,8.14.

EXAMPLE 94

N-[4-(4-Carboxybutylthio)phenyl]-3-methoxymethyl-6,7-dihydro-5H-thiazolo[3,2-a]pyrimidine-2-carboxamide hydrochloride Melting Point 234°"235° C.

Elementary Analysis for $C_{20}H_{25}N_3O_4S_2 \cdot HCl$ Calcd.: C,50.89; H,5.55; N,8.90. Found: C,50.88; H,5.56; N,8.24.

EXAMPLE 95

N-[4-(3-Ethoxycarbonylpropylthio)phenyl]-3-methoxymethyl-6,7-dihydro-5H-thiazolo[3,2-a]-pyrimidine-2-carboxamide hydrochloride Melting Point 132°"134° C.

Elementary Analysis for $C_{21}H_{27}N_3O_4S_2 \cdot HCl$ Calcd.: C,51.89; H,5.81; N,8.63. Found: C,51.38; H,5.73; N,8.51.

EXAMPLE 96

N-[4-(3-Carboxypropylthio)phenyl]-3-methoxymethyl-6,7-dihydro-5H-thiazolo[3,2-a]pyrimidine-2-carboxamide hydrochloride Melting Point 225° C.

EXAMPLE 97

N-[4-(5-Ethoxycarbonylpentyloxy)phenyl]-3-methoxymethyl-6,7-dihydro-5H-thiazolo[3,2-a]-pyrimidine-2-carboxamide hydrochloride Melting Point 140°"141° C.

Elementary Analysis for $C_{23}H_{31}N_3O_5S \cdot HCl$ Calcd.: C,55.46; H,6.48; N,8.43. Found: C,55.78; H,6.33; N,8.42.

EXAMPLE 98

N-[4-(5-Carboxypentyloxy)phenyl]-3-methoxymethyl-6,7-dihydro-5H-thiazolo[3,2-a]pyrimidine-2-carboxamide hydrochloride Melting Point 240°"241° C.

Elementary Analysis for $C_{21}H_{27}N_3O_5S \cdot HCl$ Calcd.: C,53.66; H,6.01; N,8.94. Found: C,53.90; H,6.03; N,8.30.

EXAMPLE 99

N-[4-{1-(1-Ethoxycarbonyl)pentylthio}phenyl]-3-methoxymethyl-6,7-dihydro-5H-thiazolo[3,2-a]-pyrimidine-2-carboxamide hydrochloride Melting Point 132°"135° C.

Elementary Analysis for $C_{23}H_{31}N_3O_4S_2 \cdot HCl$ Calcd.: C,53.73; H,6.27; N,8.17. Found: C,53.74; H,6.21; N,8.14.

EXAMPLE 100

N-[4-{1-(1-Carboxy)Pentylthio}phenyl]-3-methoxymethyl-6,7-dihdyro-5H-thiazolo[3,2-a]-pyrimidine-2-carboxamide hydrochloride Melting Point 202°"205° C.

Elementary Analysis for $C_{21}H_{27}N_3O_4S_2 \cdot HCl$ Calcd.: C,51.89; H,5.81; N,8.65. Found: C,51.67; H,5.72; N,8.29.

EXAMPLE 101

N-[4-(2-t-Butoxycarbonylethylthio)phenyl]-3-ethoxymethyl-6,7-dihydro-5H-thiazolo[3,2-a]-pyrimidine-2-carboxamide hydrochloride Melting Point 192°"193° C.

Elementary Analysis for $C_{23}H_{31}N_3O_4S_2 \cdot HCl$ Calcd.: C,53.73; H,6.27; N,8.17. Found: C,53.40; H,6.27; N,8.16.

EXAMPLE 102

N-[4-(2-Carboxyethylthio)phenyl]-3-ethoxymethyl-6,7-dihydro-5H-thiazolo[3,2-a]pyrimidine-2-carboxamide hydrochloride Melting Point 197° C.

Elementary Analysis for $C_{19}H_{23}N_3O_4S_2 \cdot HCl$ Calcd.: C,49.82; H,5.28; N,9.18. Found: C,49.68; H,5.24; N,9.16.

EXAMPLE 103

N-[4-(3-Ethoxycarbonylpropylthio)phenyl]-3-ethoxymethyl-6,7-dihydro-5H-thiazolo[3,2-a]-pyrimidine-2-carboxamide hydrochloride Melting Point 131°"132° C.

Elementary Analysis for $C_{22}H_{29}N_3O_4S_2 \cdot HCl$ Calcd.: C,52.84; H,6.05; N,8.40. Found: C,52.52; H,6.04; N,8.38.

EXAMPLE 104

N-[4-(3-Carboxypropylthio)phenyl]-3-ethoxymethyl-6,7-dihydro-5H-thiazolo[3,2-a]pyrimidine-2-carboxamide hydrochloride Melting Point 199°"200° C.

Elementary Analysis for $C_{20}H_{25}N_3O_4S_2 \cdot HCl$ Calcd.: C,50.89; H,5.55; N,8.90. Found: C,50.12; H,5.60; N,8.80.

EXAMPLE 105

N-[3-(4-Methoxycarbonylphenyl)phenyl]-3-cyclobutyl-6,7-dihdyro-5H-hiazolo[3,2-a]pylimidine-2-carboxamide hydrochloride

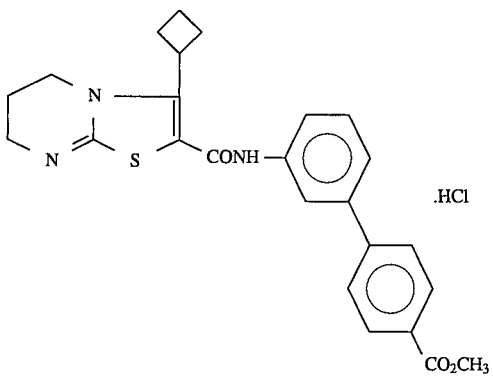

In 10 ml of pyridine were dissolved 800 mg of 3-cyclobutyl-6,7-dihydro-5H-thiazolo[3,2-a]pyrimidine-2-carboxamide hydrochloride (described in Example 2) and 620 mg of methyl 3'-amino-biphenyl-4-carboxylate obtained in Reference Example 9, followed by stirring at 80° C. for 12 hours. To the reaction mixture was added water. The solvent was removed under reduced pressure. To the residue was added isopropylalcohol and any insoluble matter was collected by filtration. The mixture was washed successively water and diethyether and dried to obtain 684 mg of the titled compound.

Melting Point 258°"260° C. $^1$H-NMR(CDCl$_3$—CD$_3$OD) δ (ppm): 1.87(1H, m), 2.12(1H, m), 2.26(2H, m), 2.32(2H, m), 2.49(2H, m), 3.62(2H, t), 3.82(1H, m), 3.96(3H, s), 4.05(2H, t), 7.48 (2H, m), 7.63(1H, m), 7.72(2H, d), 8.00(1H, m), 8.11(2H, d).

Elementary Analysis for $C_{25}H_{25}N_3O_3S \cdot HCl \cdot 0.8 \, H_2O$ Calcd.: C,60.24; H,5.58; N,8.43. Found: C,60.33; H,5.76; N,8.54.

EXAMPLE 106

N-[3-(4-Carboxyphenyl)phenyl]-3-cyclobutyl-6,7-dihydro-5H-thiazolo[3,2-a]pyrimidine-2-carboxamide hydrochloride

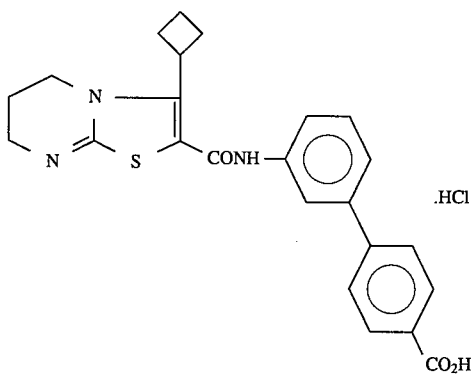

In 50 ml of 20% hydrogenchloride aqueous solution was dissolved 360 mg of N-[3-(4-methoxycarbonylphenyl)-phenyl]-3-cyclobutyl-6,7-dihydro-5H-thiazolo[3,2-a]pyrimidine-2-carboxamide hydrochloride obtained in Example 105, followed by stirring under heating 9 hours. Insoluble materials were collected by filtration. The mixture was washed with water and recrystallized from methanol-ethanol to obtain 225 mg of the titled compound.

Melting Point 291° C. $^1$H-NMR(CDCl$_3$—CD$_3$OD) δ (ppm): 1.85(1H, m), 2.10(1H, m), 2.22(2H, m), 2.32(2H, m), 2.48(2H, m), 3.60(2H, t), 3.82(1H, m), 4.06(2H, t), 7.48(2H, m), 7.65(1H, m), 7.72(2H, d), 7.98(1H, m), 8.10(2H, m).

Elementary Analysis for $C_{24}H_{23}N_3O_3S \cdot HCl$ Calcd.: C,61.33; H,5.15; N,8.94. Found: C,60.83; H,5.26 ; N,8.84.

The following compounds of Example 107 to 109 were prepared in a similar manner as described in Example 105 and 106.

EXAMPLE 107

N-[4-(4-tert-Butoxycarbonylphenyl)phenyl]-3-cyclobutyl-6,7-dihydro-5H-thiazolo[3,2-a]-pyrimidine-2-carboxamide hydrochloride Melting Point over 307° C. (decomposition) $^1$H-NMR (CDCl$_3$—CD$_3$OD ) δ (ppm): 1.63(9H, s), 1.89(1H, m), 2.13(1H, m), 2.25(2H, m), 2.32(2H, m), 2.48(2H, m), 3.61(2H, t), 3.80(1H, m), 4.05(2H, t), 7.67(4H, d), 7.76(2H, d), 8.04(2H, d).

Elementary Analysis for $C_{28}H_{31}N_3O_3S \cdot HCl$ Calcd.: C,63.93; H,6.13; N,7.99. Found: C,63.48; H,6.21; N,8.02.

EXAMPLE 108

N-[4-(4-Carboxyphenyl)phenyl]-3-cyclobutyl-6,7-dihydro-5H-thiazolo[3,2-a]pyrimidine-2-carboxamide trifluoroacetate Melting Point 244°"248° C. $^1$H-NMR(DMSO-d$_6$) δ (ppm): 1.75(1H, m), 1.97(1H, m), 2.09(2H, m), 2.19(2H, m), 2.47(2H, m), 3.53(2H, t), 3.82(1H, m), 4.02(2H, t), 7.75(6H, m), 8.02(2H, d), 10.52(1H, br), 10.70(1H, s).

Elementary Analysis for $C_{24}H_{23}N_3O_3S \cdot CF_3COOH \cdot 0.4 \, H_2O$ Calcd.: C,56.29; H,4.51; N,7.57. Found: C,56.33; H,4.70; N,7.50.

EXAMPLE 109

N-[3-(4-Methoxycarbonylphenyl)phenyl]-3-methyl-6,7-dihydro-5H-thiazolo[3,2-a]pyrimidine-2-carboxamide hydrochloride Melting Point 260°"264° C. $^1$H-NMR(CDCl$_3$—CD$_3$OD) δ (ppm): 2.32(2H, m), 2.62(3H, s), 3.65(2H, t), 3.96(3H, s), 4.14(2H, t), 7.48(2H, m), 7.62(1H, m), 7.72(2H, d), 7.97(1H, m), 8.10(2H, d)).

Elementary Analysis for $C_{22}H_{21}N_3O_3S \cdot HCl$ Calcd.: C,59.52; H,5.00; N,9.47. Found: C,59.08; H,5.14; N,9.54.

EXAMPLE 110

Ethyl 2-(3,5-dichlorophenylaminocarbonyl)acetate

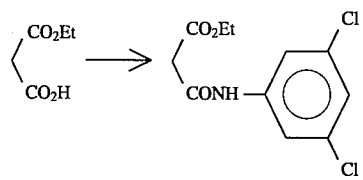

In 200 ml of methylene chloride were dissolved 5.0 g of monoethylmalonate and 6.12 g of 3,5-dichloroaniline. Under cooling with ice, to the mixture was added 8.57 of N,N'-dicyclohexylcarbodiimide, followed by stirring at room temperature for 5 hours. Insoluble materials were removed by filtration. The filtrate was diluted with ethyl acetate, washed with 1N hydrochloric acid and dried over anhydrous magnesium sulfate. The residue was purified by silica gel column chromatography (silica gel:250 g) using a mixed solvent of chloroform and acetone (20:1 by volume) to obtain 6.57 g of the oily titled comouond.

$^1$H-NMR(CDCl$_3$) δ (ppm): 1.33(3H, t), 3.47(2H, s), 4.62(2H, q), 7.10(1H, t), 7.53(2H, d).

EXAMPLE 111

N-(3,5-Dichlorophenyl)-6,7-dihydro-3-hydroxy-5H-thiazolo[3,2-a]pyrimidine-2-carboxamide

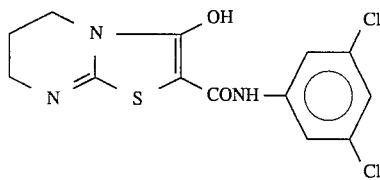

In 4 ml of carbon tetrachloride was dissolved 5.99 g of ethyl 2-(3,5-dichlorophenylaminocarbonyl) acetate obtained in Example 110. To the solution was added dropwise 1.4 ml of bromine at temperature of from 40° C. to 50° C., followed by reflux under heating for 1 hour. To the mixture was added diethylether and insoluble materials were removed by filtration. The filtrate was washed with successively water, saturated sodium hydrogencarbonate aqueous solution and saturated sodium chloride aqueous solution, and dried over anhydrous magnesium sulfate. The solvent was removed under reduced pressure to obtain an oily pale brown compound. The oily substance was dissolved in 50 ml of methylethylketone. To the solution was added 2.15 g of 3,4,5,6-tetrahydro-2-pylimidinethiol, followed by reflux under heating for 90 minutes. The solvent was under removed reduced pressure. The residue was purified by silica gel column chromatography (silica gel:250 g) using a mixed solvent of chloroform and methanol (20:1 by volume) to obtain 1.38 g of the titled compound.

Melting Point 270°"272° C. $^1$H-NMR(DMSO-d$_6$) δ (ppm): 2.04(2H, m), 3.48(2H, m), 3.75(2H, t), 7.00(1H, t), 7.58(2H, d), 10.04(1H, br), 10.16(1H, s).

Elementary Analysis for C$_{13}$H$_{11}$Cl$_2$N$_3$O$_2$S.0.5 H$_2$O Calcd.: C,44.21; H,3.42; N,11.90. Found: C,44.12; H,3.29; N,11.75.

EXAMPLE 112

N-(3,5-Dichlorophenyl)-6,7-dihydro-3-methoxy-5H-thiazolo[3,2-a]pyrimidine-2-carboxamide

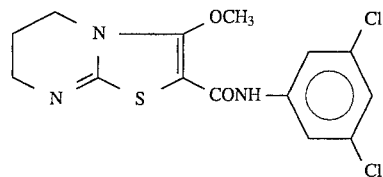

In 20 ml of tetrahydrofuran was dissolved 380 mg of triphenyl phosphin. Under cooling with ice, to the solution was added 228 µl of azodicarboxylic acid diethylester, followed by cooling to −78° C. To the mixture was added 500 mg of N-(3,5-dichlorophenyl)-6,7-dihydro-3-hydroxy-5H-thiazolo[3,2a-]pyrimidine-2-carboxamide obtained in Example 111 and 70 µl methanol, and the reaction temperature was raised to room temperature by the degree. To the mixture was added a solution of 380 mg of triphenylphosphine, the solution of 228 µl of azodicarboxylic acid diethylester in 5ml of tetrahydrofuran and 70 µl of methanol under cooling with ice. The reaction mixture was stirred at the same temperature for 1 hour. To the mixture was added diethylether. Insoluble materials were removed by filtration. The filtrate was washed with diethylether and dried to obtain 428 mg of the titled compound.

Melting Point over 300° C. (decomposition) $^1$H-NMR(DMSO-d$_6$) δ (ppm): 2.11(2H, m), 3.14(3H, s), 3.57(2H, t), 3.69(2H, t), 7.07(1H, t), 7.62(2H, d), 10.13(1H, s).

Elementary Analysis for C$_{14}$H$_{13}$Cl$_2$N$_3$O$_2$S Calcd.: C,46.94; H,3.66; N,11.73. Found: C,46.87; H,3.42; N,11.43.

EXAMPLE 113

N-(3,5-Dichlorophenyl)-6,7-dihydro-3-ethoxycarbonylmethoxy-5H-thiazolo[3,2-a]-pyrimidine-2-carboxamide

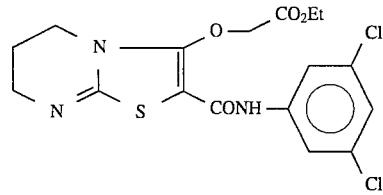

In 40 ml of tetrahydrofuran was dissolved 916 mg of triphenylphosphin. To the solution was added 550 µl of azodicarboxylic acid diethylester under cooling with ice, followed by cooling to −78° C. To the reaction mixture was added 1.0 g of N-(3,5-dichlorophenyl)-6,7-dihydro-3-hydroxy-5H-thiazolo[3,2-a]pyrimidine-2-carboxamide obtained in Example 111 and 400 µl of hydroxyacetic acid ethylester, followed by raising the reaction temperature to room temperature by the degree. After stirring at room temperature for 1 hour, the solvent was removed under reduced pressure. The residue was purified by silica gel column chromatography (silica gel:50 g) using chloroform and metanol (20:1 by volume) as an eluent to obtain 1.00 g of the titled compound.

Melting Point 165°"170° C. $^1$H-NMR(CDCl$_3$) δ (ppm): 1.33(3H, t), 2.31(2H, m), 3.69(2H, m), 3.93(2H, t), 4.19(2H, s), 4.29(2H, q). 6.99(1H, t), 7.63(2H, d).

Elementary Analysis for C$_{17}$H$_{17}$Cl$_2$N$_3$O$_4$S.0.5 CHCl$_3$ Calcd.: C,42.90; H,3.60; N,8.58. Found: C,43.08; H,3.28; N,8.55.

EXAMPLE 114

N-(3,5-Dichlorophenyl)-3-carboxymethyloxy-6,7-dihydro-5H-thiazolo[3,2-a]pyrimidine-2-carboxamide

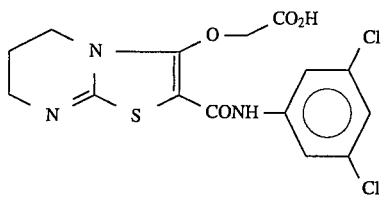

In 8 ml of ethanol was suspended 650 mg of N-(3,5-dichlorophenyl)-6,7-dihydro-3-ethoxycarbonylmethoxy-5H-thiazolo[3,2-a]pyrimidine-2-carboxamide obtained in Example 113. To the suspension was added 2 ml of 1N sodium hydroxide aqueous solution at room temperature, followed by stirring at the same temperature for 30 minutes. The mixure was made acidic with a concentrated hydrochloric acid. The precipitated crystals were collected by filtration, washed with water and diethylether, and dried to obtain 484 mg of the titled compound.

Melting Point 247°"252° C. $^1$H-NMR(DMSO-d$_6$) δ (ppm): 2.13(2H, m), 3.63(2H, t), 3.77(2H, t), 4.34(2H, s), 7.07(1H, t), 7.62(2H, t), 10.09(1H, s).

Elementary Analysis for C$_{15}$H$_{13}$N$_3$O$_4$S Calcd.: C,44.79; H,3.25; N,10.45. Found: C,44.86; H,3.18; N,10.36.

The following compounds of Example 115 to 118 were prepared in a similar manner as described in Example 111 to 114.

EXAMPLE 115

N-(n-Octylphenyl)-6,7-dihydro-3-hydroxy-5H-thiazolo[3,2a]-pyrimidine-2-carboxamide Melting Point 203°–210° C. $^1$H-NMR(CDCl$_3$) δ (ppm): 0.87(3H, t), 1.26(10H, m), 1.56(2H, m), 1.95(2H, m), 2.54(2H, m), 3.12(3H, s). 3.81(2H, t), 7.09(2H, d), 7.39(2H, d), 9.95(1H, br).

Elementary Analysis for C$_{21}$H$_{29}$N$_3$O$_2$S.H$_2$O Calcd.: C,62.19; H,7.64; N,10.36. Found: C,62.37; H,7.31; N,10.65.

EXAMPLE 116

N-(n-Octylphenyl)-6,7-dihydro-methoxy-5H-thiazolo[3,2-a]-pyrimidine-2-carboxamide Melting Point 203°–210° C. $^1$H-NMR(CDCl$_3$) δ (ppm): 0.87(3H, t), 1.26(10H, m), 1.58(2H, m), 2.23(2H, m), 2.54(2H, m), 3.14(3H, s). 3.52(2H, t), 3.87(2H, t), 7.08(2H, d), 7.53(2H, m), 9.74(1H, br).

Elementary Analysis for C$_{22}$H$_{31}$N$_3$O$_2$S.0.5 H$_2$O Calcd.: C,64.36; H,7.86; N,10.23. Found: C,64.02; H,7.71; N,10.46.

EXAMPLE 117

N-(3,5-Dichlorophenyl)-3-aryloxy-6,7-dihydro-5H-thiazolo[3,2-a]pyrimidine-2-carboxamide Melting Point 240°–246° C. $^1$H-NMR(CDCl$_3$) δ (ppm): 2.26(2H, m), 3.61(2H, br), 3.91(2H, br), 4.08(2H, br), 5.44(2H, m), 5.82(1H, m). 6.99(1H, br), 7.65(2H, br).

Elementary Analysis for C$_{16}$H$_{15}$Cl$_2$N$_3$O$_2$S Calcd.: C,50.00; H,3.93; N,10.93. Found: C,49.83; H,3.91; N,10.64.

EXAMPLE 118

N-(3,5-Dichlorophenyl)-3-dodecanyloxy-6,7-dihydro-5H-thiazolo[3,2-a]pyrimidine-2-carboxamide Melting Point 139°"141° C. $^1$H-NMR(CDCl$_3$) δ (ppm): 0.88(3H, t), 1.80(2H, m), 2.32(2H, m), 3.59(2H, m), 3.80(2H, m). 3.99(2H, m), 7.07(1H, t), 7.75(2H, d).

Elementary Analysis for C$_{25}$H$_{35}$Cl$_2$N$_3$O$_2$S Calcd.: C,58.59; H,6.88; N,8.20. Found: C,58.30; H,6.69; N,8.04.

EXAMPLE 119 tert-Butyl 3,6,6-trimethyl-6,7-dihydro-5H-thiazolo[3,2-a]-pyrimidine-2-carboxylate hydrochloride

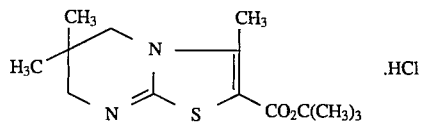

In 30 ml of anhydrous diethylether was dissolved 1.6 g of tert-butylacetoacetate. Under cooling with ice, to the solution was added dropwise 1.0 ml of sulfurylchloride. The reaction mixture was stirred at room temperature for 30 minutes. The organic layer was washed with ice-cooled 5% sodium hydrogencarbonate aqueous solution. The organic layer was separated and dried over anhydrous magnesium sulfate. The solvent was removed under reduced pressure to obtain 1.58 g of an oily residue. This residue was dissolved in 50 ml of methylethylketone. To the solution was added 1.4 g of 5,5-dimethyl-3,4,5,6-tetrahydro-2-pyrimidinethiol, followed by reflux under heating for 12 hours. The reaction mixture was cooled and the precipitated crystals were collected by filtration. The crystals were washed successively diethylether and acetone and suspended in 30 ml of isopropylalcohol, followed by reflux under heating for 12 hours. The solvent was removed under reduced pressure. To the residue was added diethylether. The precipitated crystals were collected by filtration and washed with acetone to obtain 2.2 g of the titled compound.

EXAMPLE 120

3,6,6-Trimethyl-6,7-dihydro-5H-thiazolo[3,2-a]-pyrimidine-2-carboxylic acid hydrochloride

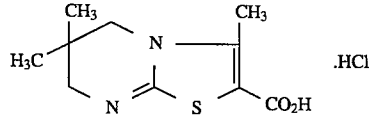

In 100 ml of 2N hydrochloric acid was suspended 2.0 g of tert-butyl 3,6,6-trimethyl-6,7-dihydro-5H-thiazolo[3,2-a]-pyrimidine-2-carboxylate hydrochloride obtained in Example 119, followed by stirring at room temperature for 7 hours. The precipitated crystals were collected by filtration and washed with diethylether and acetone to obtain 1.3 g of the titled compound.

$^1$H-NMR(D$_2$O) δ (ppm): 1.20(6H, s), 2.64(3H, s), 3.30, 3.80(each 2H, s).

EXAMPLE 121

N-(3,5-Dimethylphenyl)-3,6,6-trimethyl-6,7-dihydro-5H-thiazolo[3,2-a]pyrimidine-2-carboxamide hydrochloride

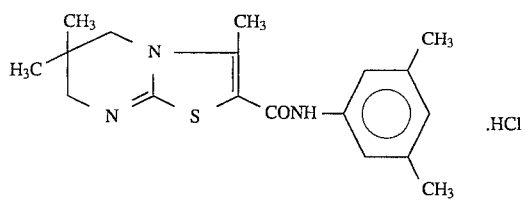

In 6 ml of thionylchloride was suspended 1.0 g of 3,6,6-trimethyl-6,7-dihydro-5H-thiazolo[3,2-a]pyrimidine-2-carboxylic acid hydrochloride obtained in Example 120, followed by reflux under heating for 30 minutes. After dissolving completely, the mixture was cooled. Under cooling with ice, to the mixture was added anhydrous diethylether. The precipitated crystals were collected by filtration and dried under reduced pressure to obtain 1.06 g of 3,6,6-trimethyl-6,7-dihydro-5H-thiazolo[3,2-a]pyrimidine-2-carbonylchloride hydrochloride. The total amount of this compound and 610 mg of 3,5-dimethylaniline was dissolved in the mixture 60 ml of pyridine and 10 ml of dimethylformamide, followed by stirring at 60° C. for 17 hours. The reaction mixture was concentrated and to the concentrate was added 5% sodium hydrogencarbonate aqueous solution. The precipitated crystals were collected by filtration and washed diethylether. The obtained powder was suspended in diethylether. To the suspension was added 0.2 ml of saturated hydrogenchloride dioxane solution, followed by stirring at room temperature. The precipitated crystals were collected by filtration. The crystals were recrystallized from a mixed solvent of ethanol and diethylether to obtain 810 mg of the titled compound.

Melting Point 279°"281° C. $^1$H-NMR(D$_2$O) δ (ppm): 1.20(6H, s), 2.51(3H, s), 3.30, 3.85(each 2H, s), 7.40–7.51(3H, m).

Elementary Analysis for C$_{16}$H$_{17}$N$_3$OSCl.HCl Calcd.: C,47.24; H,4.46; N,10.33. Found: C,47.49; H,4.44; N,10.45.

Following compound of Example 112 was prepared in a similar manner as described in Example 121.

EXAMPLE 122

N-(n-Octyl)-3,6,6-trimethyl-6,7-dihydro-5H-thiazolo[3,2-a]-pyrimidine-2-carboxamide hydrochloride Melting Point 178°"179° C.

Elementary Analysis for C$_{18}$H$_{31}$N$_3$OS.HCl Calcd.: C,57.81; H,8.62; N,11.24. Found: C,57.81; H,8.82; N,11.26.

Angiogenesis inhibition test

Test was carried out by Tayler-Folkman's method (Nature, 297, 307 (1982)), but partially modified as described in Exp. Path. 30, 143 (1986). Chorioallantoic membrance (CAM) of 4 to 5 day old fertilized chicken egg (Babucock) was exposed. To the CAM, test sample dissolved in physiological saline or dimethylsulfoxide (DMSO) was added (10 μl/egg) and the egg was incubated at 37.6° C. Two days after, the antiangiogenesis activity was determined in compared with control group which did not contain the test compound. Vascularization (angiogenesis) of the control group was settled as 100 and the degree to the test sample was calcurated and expressed as inhibition activity. The significance of activity was determined by Student's t-test and the case over 50 % was indicated to + and the case below 50 % to i as shown in the following table.

| CAM angiogenesis Inhibition Test | | |
|---|---|---|
| Example No. | Inhibition activity (%) | Judgement |
| Example 2 | 82.5 | + |
| Example 8 | 82.7 | + |
| Example 9 | 37.2 | ± |
| Example 13 | 76.5 | + |
| Example 16 | 57.1 | + |
| Example 19 | 69.3 | + |
| Example 39 | 32.3 | ± |
| Example 82 | 88.4 | + |
| Example 90 | 93.2 | + |
| Example 114 | 94.3 | + |

TABLE 1

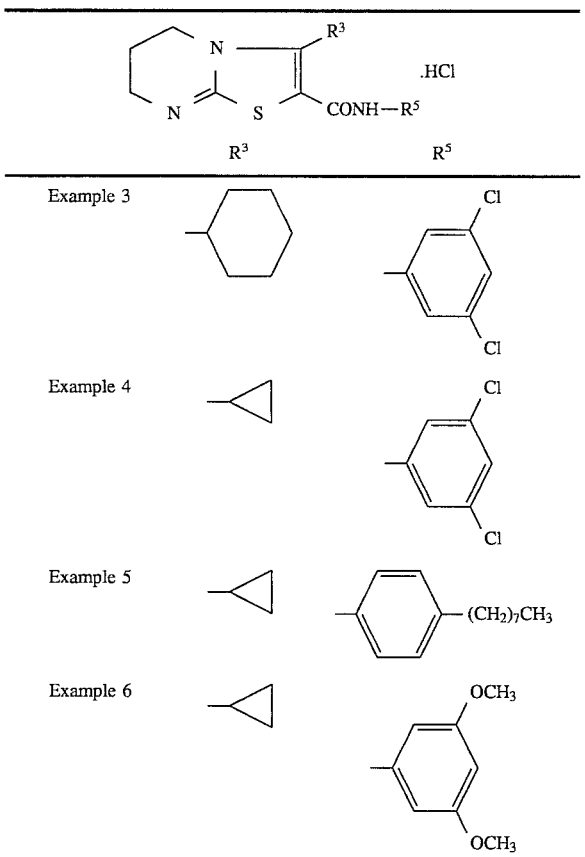

TABLE 1-continued

Structure: tetrahydropyrimidine-thiazole with R³ and CONH-R⁵ substituents, ·HCl salt

| | R³ | R⁵ |
|---|---|---|
| Example 7 | cyclobutyl | –C₆H₄–(CH₂)₉CH₃ (para) |
| Example 8 | cyclobutyl | –C₆H₄–(CH₂)₇CH₃ (para) |
| Example 9 | cyclopentyl | –C₆H₃(Cl)₂ (3,5-dichlorophenyl) |
| Example 10 | phenyl | –C₆H₃(Cl)₂ (3,5-dichlorophenyl) |

TABLE 2

Structure: tetrahydropyrimidine-thiazole with R³ and CONH-R⁵ substituents, ·HCl salt

| | R³ | R⁵ |
|---|---|---|
| Example 14 | –(CH$_2$)$_2$CH$_3$ | 3,5-dimethoxyphenyl |
| Example 15 | –(CH$_2$)$_2$CH$_3$ | 4-nitrophenyl |
| Example 16 | –(CH$_2$)$_2$CH$_3$ | 4-tert-butylphenyl |
| Example 17 | –(CH$_2$)$_2$CH$_3$ | 4-methoxyphenyl |
| Example 18 | –(CH$_2$)$_2$CH$_3$ | 2-methoxyphenyl |

TABLE 2-continued

| | R³ | R⁵ |
|---|---|---|
| Example 19 | –(CH$_2$)$_2$CH$_3$ | –C$_6$H$_4$–(CH$_2$)$_7$CH$_3$ (para) |
| Example 20 | –(CH$_2$)$_2$CH$_3$ | 2,5-dichloro-4-sulfophenyl |
| Example 21 | –(CH$_2$)$_2$CH$_3$ | –C$_6$H$_4$–(CH$_2$)$_9$CH$_3$ (para) |
| Example 22 | –(CH$_2$)$_2$CH$_3$ | –C$_6$H$_4$–(CH$_2$)$_3$CH$_3$ (para) |
| Example 23 | –(CH$_2$)$_2$CH$_3$ | –C$_6$H$_4$–(CH$_2$)$_5$CH$_3$ (para) |
| Example 24 | –(CH$_2$)$_2$CH$_3$ | –C$_6$H$_4$–(CH$_2$)$_2$CH$_3$ (para) |
| Example 25 | –(CH$_2$)$_2$CH$_3$ | phenyl |

TABLE 3

Structure: tetrahydropyrimidine-thiazole with R³ and CONH-R⁵ substituents, ·HCl salt

| | R³ | R⁵ |
|---|---|---|
| Example 29 | –CH$_3$ | –C$_6$H$_4$–(CH$_2$)$_3$CH$_3$ (para) |
| Example 30 | –CH$_3$ | –C$_6$H$_4$–CH$_3$ (para) |
| Example 31 | –CH$_3$ | –C$_6$H$_4$–CH$_2$CH$_3$ (para) |
| Example 32 | –CH$_3$ | –C$_6$H$_4$–(CH$_2$)$_2$CH$_3$ (para) |

TABLE 3-continued

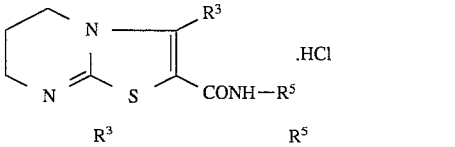
·HCl

| | R³ | R⁵ |
|---|---|---|
| Example 33 | —CH₃ | 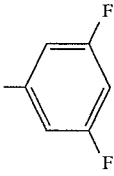 3,5-F₂-phenyl |
| Example 34 | —CH₃ | 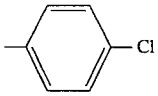 4-Cl-phenyl |
| Example 35 | —CH₃ | 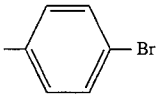 4-Br-phenyl |

TABLE 4

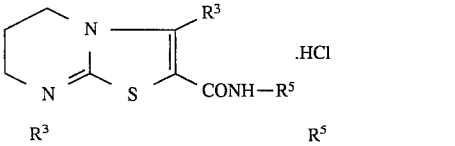
·HCl

| | R³ | R⁵ |
|---|---|---|
| Example 38 | —(CH₂)₃CH₃ | 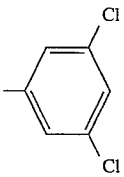 3,5-Cl₂-phenyl |
| Example 39 | —(CH₂)₃CH₃ | 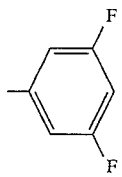 3,5-F₂-phenyl |
| Example 40 | —CH₂CH₃ | 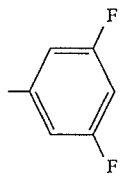 3,5-F₂-phenyl |
| Example 41 | —CH₂CH₃ | 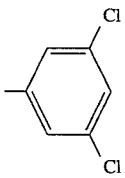 3,5-Cl₂-phenyl |

TABLE 4-continued

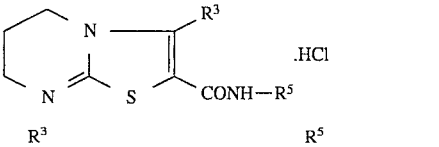
·HCl

| | R³ | R⁵ |
|---|---|---|
| Example 42 | —CH₂CH₃ | 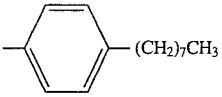 4-(CH₂)₇CH₃-phenyl |
| Example 43 | —CH₂CH₃ | 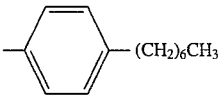 4-(CH₂)₆CH₃-phenyl |
| Example 45 | —(CH₂)₁₂CH₃ | 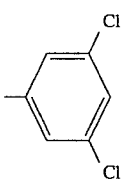 3,5-Cl₂-phenyl |

TABLE 5

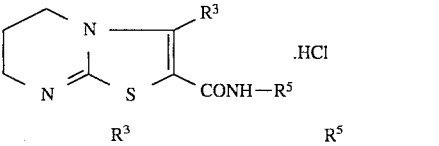
·HCl

| | R³ | R⁵ |
|---|---|---|
| Example 48 | —CH(CH₃)₂ |  3,5-Cl₂-phenyl |
| Example 49 | —CH(CH₃)₂ | 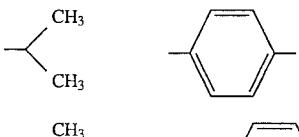 4-OCH₃-phenyl |
| Example 50 | —CH(CH₃)₂ | 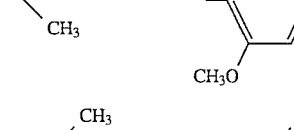 3-OCH₃-phenyl |
| Example 51 | —CH(CH₃)CH₂CH₃ | 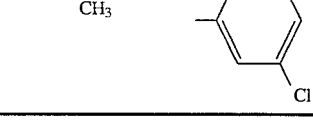 3,5-Cl₂-phenyl |

TABLE 6

Structure: tetrahydropyrimidine-thiazole with R³ on C=C, CON(R⁴)R⁵, ·HCl

| | R³ | R⁴ | R⁵ |
|---|---|---|---|
| Example 53 | cyclopropyl | —CH₃ | 2,4-dichlorophenyl |
| Example 54 | —(CH₂)₃CH₃ | —CH₃ | 2,4-dichlorophenyl |
| Example 55 | cyclohexyl | —CH₃ | 2,4-dichlorophenyl |
| Example 56 | —(CH₂)₄CH₃ | —CH₃ | 2,4-dichlorophenyl |
| Example 59 | —(CH₂)₂CH₃ | —(CH₂)₂OH | 2,4-dichlorophenyl |
| Example 60 | —(CH₂)₂CH₃ | —(CH₂)₂CN | 2,4-dichlorophenyl |

TABLE 7

Structure: tetrahydropyrimidine-thiazole with R³ on C=C, CONH—R⁵

| | R³ | R⁵ |
|---|---|---|
| Example 62 | —CH₃ | 3-pyridyl |
| Example 63 | —CH₃ | —(CH₂)₂—piperidino |
| Example 64 | —CH₃ | —(CH₂)₂—(2-pyridyl) |
| Example 65 | —CH₃ | —(CH₂)₂—pyrrolidino |
| Example 66 | —CH₃ | —(CH₂)₂—morpholino |
| Example 67 | —CH₃ | thiazolin-2-yl |
| Example 68 | —CH₃ | 1,3,4-thiadiazol-2-yl |
| Example 69 | —CH₃ | benzothiazol-2-yl |
| Example 70 | —CH₃ | 5-chlorobenzothiazol-2-yl |

Note: The compounds of Examples 62 to 66 are dihydrochlorides and the compounds of Examples 67 to 70 are monohydrochlorides.

TABLE 8

Structure: tetrahydropyrimidine-thiazole with R³ on C=C, CONH—R⁵

| | R³ | R⁵ |
|---|---|---|
| Example 72 | —CH₃ | —(CH₂)₈CH=CH—(CH₂)₇CH₃ |
| Example 73 | cyclopropyl | —(CH₂)₈CH=CH—(CH₂)₇CH₃ |
| Example 74 | —CH₃ | —(CH₂)₁₇CH₃ |
| Example 75 | —CH₃ | —C(CH₃)₂CH₂C(CH₃)₃ |
| Example 76 | —CH₃ | —(CH₂)₇CH₃ |

Note: The compounds of Examples 73 to 76 are monohydrochlorides.

TABLE 9
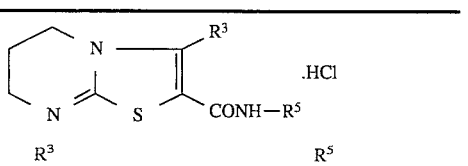
| | R³ | R⁵ |
|---|---|---|
| Example 81 | —(CH₂)₃CO₂H | 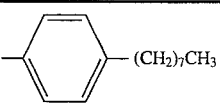 —(CH₂)₇CH₃ |
| Example 82 | —(CH₂)₂CN | 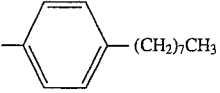 —(CH₂)₇CH₃ |
| Example 83 | —(CH₂)₃CN | 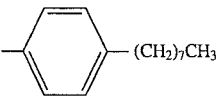 —(CH₂)₇CH₃ |
TABLE 10
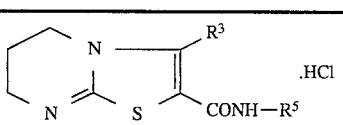
| | R³ | R⁵ |
|---|---|---|
| Example 86 | —(CH₂)₂CH₃ | 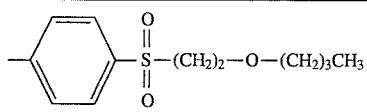 |
| Example 87 | —(CH₂)₂CH₃ | 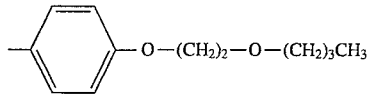 —O—(CH₂)₂—O—(CH₂)₃CH₃ |
| Example 88 | —(CH₂)₂CH₃ | 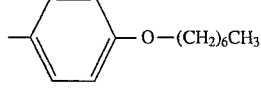 —O—(CH₂)₆CH₃ |
| Example 91 | —CH₂OCH₃ | 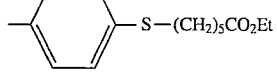 —S—(CH₂)₅CO₂Et |
| Example 92 | —CH₂OCH₃ | 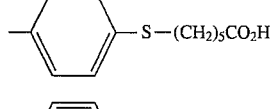 —S—(CH₂)₅CO₂H |
| Example 93 | —CH₂OCH₃ | 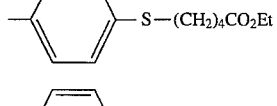 —S—(CH₂)₄CO₂Et |
| Example 94 | —CH₂OCH₃ | 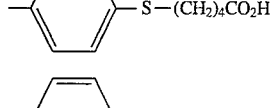 —S—(CH₂)₄CO₂H |
| Example 95 | —CH₂OCH₃ |  —S—(CH₂)₃CO₂Et |

TABLE 10-continued

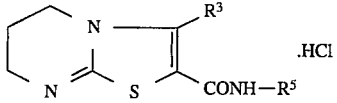

| | R³ | R⁵ |
|---|---|---|
| Example 96 | —CH₂OCH₃ | 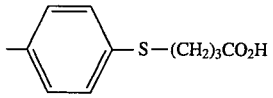 —S—(CH₂)₃CO₂H |
| Example 97 | —CH₂OCH₃ | 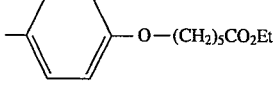 —O—(CH₂)₅CO₂Et |
| Example 98 | —CH₂OCH₃ | 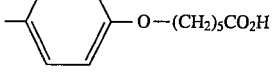 —O—(CH₂)₅CO₂H |
| Example 99 | —CH₂OCH₃ | 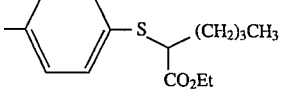 |

TABLE 11

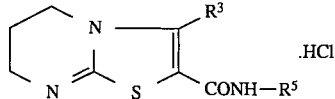

| | R³ | R⁵ |
|---|---|---|
| Example 100 | —CH₂OCH₃ | 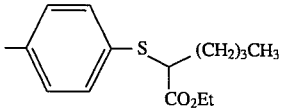 |
| Example 101 | —CH₂OCH₂CH₃ | 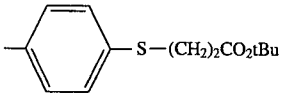 —S—(CH₂)₂CO₂tBu |
| Example 102 | —CH₂OCH₂CH₃ | 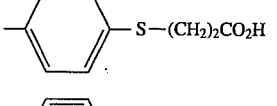 —S—(CH₂)₂CO₂H |
| Example 103 | —CH₂OCH₂CH₃ | 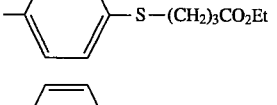 —S—(CH₂)₃CO₂Et |
| Example 104 | —CH₂OCH₂CH₃ | 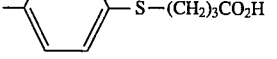 —S—(CH₂)₃CO₂H |

TABLE 12

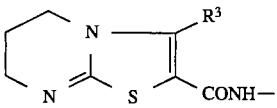

| | R³ | R⁵ |
|---|---|---|
| Example 107 | 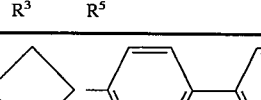 | 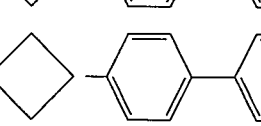 —CO₂tBu |
| Example 108 | 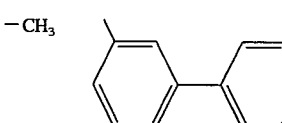 | 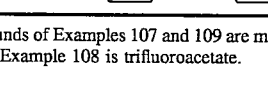 —CO₂H |
| Example 109 | —CH₃ | 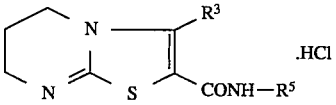 —CO₂CH₃ |

Note: The compounds of Examples 107 and 109 are monohydrochlorides and the compound of Example 108 is trifluoroacetate.

TABLE 13

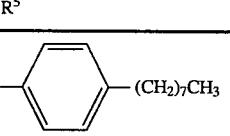

| | R³ | R⁵ |
|---|---|---|
| Example 115 | —OH | —⟨C₆H₄⟩—(CH₂)₇CH₃ |

TABLE 13-continued

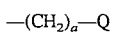

| | R³ | R⁵ |
|---|---|---|
| Example 116 | —OCH₃ | 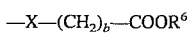 —(CH₂)₇CH₃ |
| Example 117 | —OCH₂CH=CH₂ | 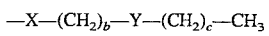 Cl, Cl |
| Example 118 | —O—(CH₂)₁₁CH₃ | Cl, Cl, Cl |

While the instant invention has been described in detail and with reference to specific embodiments thereof, it will be apparent to one skilled in the art that various changes and modifications can be made therein without departing from the spirit and scope thereof.

What is claimed is:

1. Compounds represented by the following general formula

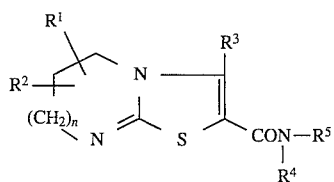

wherein n represents 1;
$R^1$ and $R^2$ each represents independently a hydrogen atom or an alkyl group having from 1 to 6 carbon atoms;
$R^3$ represents a hydroxyl group, an alkyl group having from 1 to 12 carbon atoms, a cycloalkyl group having from 3 to 6 carbon atoms, a halogenoalkyl group having from 1 to 6 carbon atoms, a cyanoalkyl group having from 2 to 7 carbon atoms, an alkoxyalkyl group having a total of from 2 to 12 carbon atoms, an alkoxycarbonylalkyl group having a total of from 3 to 10 carbon atoms, a carboxyalkyl group having a total of from 2 to 7 carbon atoms, an alkoxyl group having from 1 to 12 carbon atoms, a cycloalkoxyl group having from 3 to 6 carbon atoms, an alkoxyalkoxyl group having from 2 to 9 carbon atoms, an alkoxycarbonylalkoxyl group having from 3 to 10 carbon atoms, a carboxyalkoxyl group having from 2 to 4 carbon atoms, an alkenylalkoxyl group having from 3 to 6 carbon atoms or an aryl group having from 6 to 12 carbon atoms;
$R^4$ and $R^5$ each represents independently a hydrogen atom, an alkyl group having from 1 to 18 carbon atoms, an alkoxycarbonylalkyl group having a total of from 3 to 7 carbon atoms, a carboxyalkyl group having a total of from 2 to 4 carbon atoms, a cyanoalkyl group having from 2 to 4 carbon atoms, a hydroxyalkyl group having from 1 to 3 carbon atoms, an alkenyl group having from 2 to 18 carbon atoms, a cycloalkyl group having from 3 to 6 carbon atoms, a phenylsulfonyl group or a group of formula:

$$-(CH_2)_a-Q$$

wherein "a" represents 0 or an integer of 1 to 6;
Q represents an aryl group having from 6 to 12 carbon atoms, a heterocyclic group selected from the group consisting of pyridyl, pyrazinyl, oxazolyl, thiazolyl, thiadiazolyl, imidazolyl, pyrrolidinyl, piperidyl, and morpholinyl, or a condensed ring group selected from the group consisting of benzoxazolyl, benzothiazolyl and benzothiadiazolyl, the Q may contain simultaneously or independently 1 to 3 substitution groups selected from a halogen atom, a nitro group, a sulfo group, a group of formula:

$$-X-(CH_2)_b-COOR^6$$

or a group of formula:

$$-X-(CH_2)_b-Y-(CH_2)_c-CH_3$$

wherein X represents a single-bond, an oxygen atom, a sulfur atom, a sulfonyl group or an aryl group having from 6 to 10 carbon atoms; Y represents a single-bond, an oxygen atom, or an aryl group having from 6 to 10 carbon atoms; $R^6$ represents a hydrogen atom or an alkyl group having from 1 to 3 carbon atoms;
b and c each represents 0 or an integer of 1 to 6; if X is said aryl group, then —(CH₂)$_b$—COOR⁶, —(CH₂)$_b$—Y—(C₂)$_c$—CH₃, —COOR⁶ (when b is 0) or —Y—(CH₂)$_c$—CH₃ (when b is 0) may be substituted at any position of said aryl group, if Y is said aryl group, then —(CH₂)$_c$—CH₃ or —CH₃ (when c is 0) may be substituted at any position of said aryl group, or pharmaceutically acceptable salts thereof.

2. Compounds represented by the following general formula

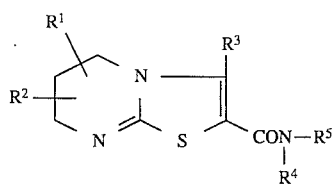

wherein $R^1$ aria $R^2$ each represents independently a hydrogen atom or an alkyl group having from 1 to 6 carbon atoms;
$R^3$ represents a hydroxyl group an alkyl group having from 1 to 12 carbon atoms, a cycloalkyl group having from 3 to 6 carbon atoms, a halogenoalkyl group having from 1 to 6 carbon atoms, a cyanoalkyl group having from 2 to 7 carbon atoms, an alkoxyalkyl group having a total of from 2 to 12 carbon atoms, an alkoxycarbonylalkyl group having a total of from 3 to 10 carbon atoms, a carboxyalkyl group having a total of from 2 to 7 carbon atoms, an alkoxyl group having from 1 to 12 carbon atoms, a cycloalkoxyl group having from 3 to 6 carbon atoms, an alkoxyalkoxyl group having from 2 to 9 carbon atoms, an alkoxycarbonylalkoxyl group having from 3 to 10 carbon atoms, a carboxyalkoxyl group having from 2 to 4 carbon atoms, an alkenylalkoxyl group having from 3 to 6 carbon atoms or an aryl group having from 6 to 12 carbon atoms;

$R^4$ and $R^5$ each represents independently a hydrogen atom, an alkyl group having from 1 to 18 carbon atoms, an alkoxycarbonylalkyl group having a total of from 3 to 7 carbon atoms, a carboxyalkyl group having a total of from 2 to 4 carbon atoms, a cyanoalkyl group having from 2 to 4 carbon atoms, a hydroxyalkyl group having from 1 to 3 carbon atoms, an alkenyl group having from 2 to 18 carbon atoms, a cycloalkyl group having from 3 to 6 carbon atoms, a phenylsulfonyl group or a group of formula:

$$-(CH_2)_a-Q$$

wherein "a" represents 0 or an integer of 1 to 6;

Q represents an aryl group having from 6 to 12 carbon atoms, a heterocyclic group selected from the group consisting of pyridyl, pyrazinyl, oxazolyl, thiazolyl, thiadiazolyl, imidazolyl, pyrrolidinyl, piperidyl, and morpholinyl, or a condensed ring group selected from the group consisting of benzoxazolyl, benzothiazolyl and benzothiadiazolyl, the Q may contain simultaneously or independently 1 to 3 substitution groups selected from a halogen atom, a nitro group, a sulfo group, a group of formula:

$$-X-(CH_2)_b-COOR^6$$

or a group of formula:

$$-X-(CH_2)_b-Y-(CH_2)_c-CH_3$$

wherein X represents a single-bond, an oxygen atom, a sulfur atom, a sulfonyl group or an aryl group having from 6 to 12 carbon atoms;

Y represents a single-bond, an oxygen atom, or an aryl group having from 6 to 12 carbon atoms; $R^6$ represents a hydrogen atom or an alkyl group having from 1 to 3 carbon atoms;

b and c each represents 0 or an integer of 1 to 6; if X is said aryl group, then $-(CH_2)_b-COOR^6$, $-(CH_2)_b-Y-(CH_2)_c-CH_3$, $-COOR^6$ (when b is 0) or $Y-(CH_2)_c-CH_3$ (when b is 0) may be substituted at any position of said aryl group, if Y is said aryl group, then $-(CH_2)_c-CH_3$ or $-CH_3$ (when c is 0) may be substituted at any position of said aryl group, or pharmaceutically acceptable salts thereof.

3. Compounds or pharmaceutically acceptable salts thereof as claimed in claim 2, wherein $R^1$ and $R^2$ are at the 6-position of the thiazolopyrimidine ring.

4. Compounds or pharmaceutically acceptable salts thereof as claimed in claim 3, wherein $R^4$ is (1) a hydrogen atom, (2) an alkyl group having from 1 to 6 carbon atoms, (3) an alkoxycarbonylalkyl group having a total of from 3 to 7 carbon atoms, (4) a carboxyalkyl group having a total of from 2 to 4 carbon atoms, (5) a cyanoalkyl group having from 2 to 4 carbon atoms, or (6) a hydroxyalkyl group having from 1 to 3 carbon atoms, and wherein $R^5$ is (1)' an alkyl group having from 1 to 18 carbon atoms, (2)' a alkenyl group having from 2 to 18 carbon atoms, (3)' a cycloalkyl group having from 3 to 6 carbon atoms, (4)' a phenylsulfonyl group or (5)' a group of formula:

$$-(CH_2)_a-Q.$$

5. Compounds or pharmaceutically acceptable salts thereof as claimed in claim 4, wherein $R^4$ is a hydrogen atom.

6. Compounds or pharmaceutically acceptable salts thereof as claimed in claim 5, wherein $R^5$ is a group of formula $$-(CH_2)_a-Q.$$

7. Compounds or pharmaceutically acceptable salts thereof as claimed in claim 6, wherein a is 0.

8. Compounds or pharmaceutically acceptable salts thereof as claimed in claim 7, wherein Q is an aryl group which may have substituents.

9. Compounds or pharmaceutically acceptable salts thereof as claimed in claim 8, wherein said aryl group is a phenyl group which may have substituents.

10. Compounds or pharmaceutically acceptable salts thereof as claimed in claim 9, wherein said phenyl group is substituted with a group of formula, $$-X-(CH_2)_b-Y-(CH_2)_c-CH_3.$$

11. Compounds or pharmaceutically acceptable salts thereof as claimed in claim 10, wherein X and Y each represents a single-bond.

12. Compounds or pharmaceutically acceptable salts thereof as claimed in claim 11, wherein the sum of b and c is an integer of 6 to 12.

13. An antiangiogenic composition which comprises a compound or a pharmaceutically acceptable salt thereof according to claim 1 and a pharmaceutically acceptable carrier.

* * * * *